US005496714A

United States Patent [19]
Comb et al.

[11] Patent Number: 5,496,714
[45] Date of Patent: Mar. 5, 1996

[54] MODIFICATION OF PROTEIN BY USE OF A CONTROLLABLE INTERVEINING PROTEIN SEQUENCE

[75] Inventors: Donald G. Comb, Beverly; Francine B. Perler, Brookline; William E. Jack, Rowley; Ming-Qun Xu, Beverly, all of Mass.; Robert A. Hodges, Manassas, Va.

[73] Assignee: New England Biolabs, Inc., Beverly, Mass.

[21] Appl. No.: 4,139

[22] Filed: Dec. 9, 1992

[51] Int. Cl.⁶ .............................. C12P 21/00; C12N 9/22
[52] U.S. Cl. ...................... 435/69.7; 534/199; 534/172.3
[58] Field of Search ................................ 435/69.7, 199, 435/172.3

[56] References Cited

PUBLICATIONS

Hirata et al., *J. Biol. Chem.* 256, 6726 (1990).
Kane et al., *Science* 250, 651 (1990).
Davis et al., *J. Bact.* 173, 5653 (1991).
Davis, et al. *Cell*, 71:201–210 (1992).
Perler, et al., *PNAS* 89, 5577 (1992).

*Primary Examiner*—Charles L. Patterson, Jr.
*Attorney, Agent, or Firm*—David G. Conlin; Gregory D. Williams; David S. Resnick

[57] ABSTRACT

The present invention is directed to modified proteins and methods of their production. The modified proteins comprise a controllable intervening protein sequence (CIVPS) inserted into a target protein, the CIVPS being capable of excision from the modified protein under predetermined conditions, i.e., increase in temperature, exposure to light, unblocking of amino acid residues by dephosphorylation or deglycosylation. If desired, the modified protein can be subjected to these conditions. The CIVPS may also be inserted into a region that substantially inactivates target protein activity.

36 Claims, 8 Drawing Sheets

I. Junction Similarities at upstream or 5' end of IVPSs:

```
                          5' EPS              5' IVPS
Pyrococcus sp. IVPS1:  I K I L A N        S I L P E E W V P L I K N G K V    (SEQ ID NO:30)
T.litoralis    IVSP1:  I K L L A N        S I L P N E W L P I I E N G E I    (SEQ ID NO:31)
T.litoralis    IVSP2:  K V L Y A D        S V S G E S E - - I R Q N G K I    (SEQ ID NO:32)
Yeast          TFP1:   A I L Y V G        C F A K G T N V L M A D G S I E    (SEQ ID NO:33)
M.tuberculosis recA:   K V V K N K        C L A E G T R I R D P V T G T T    (SEQ ID NO:34)
```

II. Junction Similarities at downstream or 3' end of IVPSs:

```
                          3' IVPS                3' EPS
Pyrococcus sp. IVPS1:  E B G K A G F G F L Y A H N    S Y Y G Y Y Y G Y A    (SEQ ID NO:35)
T.litoralis    IVSP1:  E N F L V G F G L L Y A H N    S Y Y G Y M G Y P      (SEQ ID NO:36)
T.litoralis    IVSP2:  E T H R F F A N N I L V H N    T D G F Y A T I P      (SEQ ID NO:37)
Yeast          TFP1:   D H Q F L L A N Q V V V H N    C G E R G N E M A      (SEQ ID NO:38)
M.tuberculosis recA:   E L H T L V A E G V V V H N    C S P P F K Q A E      (SEQ ID NO:39)
```

IVPS = Intervening Protein Sequence

EPS = External Protein Sequence

FIG. 1

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
( A ) LENGTH: 5837 base pairs

-continued ( B ) TYPE: nucleic acid
( C ) STRANDEDNESS: double
( D ) TOPOLOGY: Not Relevant ( x i ) SEQUENCE DESCRIPTION: SEQ ID NO:1:

| | | | | | | |
|---|---|---|---|---|---|---|
| GAATTCGCGA | TAAAATCTAT | TTTCTTCCTC | CATTTTTCAA | TTTCAAAAAC | GTAAGCATGA | 60 |
| GCCAAACCTC | TCGCCCTTTC | TCTGTCCTTC | CCGCTAACCC | TCTTGAAAAC | TCTCTCCAAA | 120 |
| GCATTTTTG | ATGAAAGCTC | ACGCTCCTCT | ATGAGGGTCA | GTATATCTGC | AATGAGTTCG | 180 |
| TGAAGGGTTA | TTCTGTAGAA | CAACTCCATG | ATTTCGATT | TGGATGGGGG | TTTAAAAATT | 240 |
| TGGCGGAACT | TTTATTTAAT | TTGAACTCCA | GTTTATATCT | GGTGGTATTT | ATGATACTGG | 300 |
| ACACTGATTA | CATAACAAAA | GATGGCAAGC | CTATAATCCG | AATTTTTAAG | AAAGAGAACG | 360 |
| GGGAGTTTAA | AATAGAACTT | GACCCTCATT | TTCAGCCCTA | TATATATGCT | CTTCTCAAAG | 420 |
| ATGACTCCGC | TATTGAGGAG | ATAAAGGCAA | TAAAGGGCGA | GAGACATGGA | AAAACTGTGA | 480 |
| GAGTGCTCGA | TGCAGTGAAA | GTCAGGAAAA | AATTTTGGG | AAGGGAAGTT | GAAGTCTGGA | 540 |
| AGCTCATTTT | CGAGCATCCC | CAAGACGTTC | CAGCTATGCG | GGGCAAAATA | AGGGAACATC | 600 |
| CAGCTGTGGT | TGACATTTAC | GAATATGACA | TACCCTTTGC | CAAGCGTTAT | CTCATAGACA | 660 |
| AGGGCTTGAT | TCCCATGGAG | GGAGACGAGG | AGCTTAAGCT | CCTTGCCTTT | GATATTGAAA | 720 |
| CGTTTTATCA | TGAGGGAGAT | GAATTTGGAA | AGGGCGAGAT | AATAATGATT | AGTTATGCCG | 780 |
| ATGAAGAAGA | GGCCAGAGTA | ATCACATGGA | AAAATATCGA | TTTGCCGTAT | GTCGATGTTG | 840 |
| TGTCCAATGA | AAGAGAAATG | ATAAAGCGTT | TTGTTCAAGT | TGTTAAAGAA | AAAGACCCCG | 900 |
| ATGTGATAAT | AACTTACAAT | GGGGACAATT | TTGATTTGCC | GTATCTCATA | AAACGGGCAG | 960 |
| AAAAGCTGGG | AGTTCGGCTT | GTCTTAGGAA | GGGACAAAGA | ACATCCCGAA | CCCAAGATTC | 1020 |
| AGAGGATGGG | TGATAGTTTT | GCTGTGGAAA | TCAAGGGTAG | AATCCACTTT | GATCTTTTCC | 1080 |
| CAGTTGTGCG | AAGGACGATA | AACCTCCCAA | CGTATACGCT | TGAGGCAGTT | TATGAAGCAG | 1140 |
| TTTTAGGAAA | AACCAAAAGC | AAATTAGGAG | CAGAGGAAAT | TGCCGCTATA | TGGGAAACAG | 1200 |
| AAGAAAGCAT | GAAAAAACTA | GCCCAGTACT | CAATGGAAGA | TGCTAGGGCA | ACGTATGAGC | 1260 |
| TCGGGAAGGA | ATTCTTCCCC | ATGGAAGCTG | AGCTGGCAAA | GCTGATAGGT | CAAAGTGTAT | 1320 |
| GGGACGTCTC | GAGATCAAGC | ACCGGCAACC | TCGTGGAGTG | GTATCTTTTA | AGGGTGGCAT | 1380 |
| ACGCGAGGAA | TGAACTTGCA | CCGAACAAAC | CTGATGAGGA | AGAGTATAAA | CGGCGCTTAA | 1440 |
| GAACAACTTA | CCTGGGAGGA | TATGTAAAAG | AGCCAGAAAA | AGGTTTGTGG | GAAAATATCA | 1500 |
| TTTATTTGGA | TTTCCGCAGT | CTGTACCCTT | CAATAATAGT | TACTCACAAC | GTATCCCCAG | 1560 |
| ATACCCTTGA | AAAAGAGGGC | TGTAAGAATT | ACGATGTTGC | TCCGATAGTA | GGATATAGGT | 1620 |
| TCTGCAAGGA | CTTTCCGGGC | TTTATTCCCT | CCATACTCGG | GGACTTAATT | GCAATGAGGC | 1680 |
| AAGATATAAA | GAAGAAAATG | AAATCCACAA | TTGACCCGAT | CGAAAAGAAA | ATGCTCGATT | 1740 |
| ATAGGCAAAG | GGCTATTAAA | TTGCTTGCAA | ACAGCATCTT | ACCCAACGAG | TGGTTACCAA | 1800 |
| TAATTGAAAA | TGGAGAAATA | AAATTCGTGA | AAATTGGCGA | GTTTATAAAC | TCTTACATGG | 1860 |
| AAAAACAGAA | GGAAAACGTT | AAAACAGTAG | AGAATACTGA | AGTTCTCGAA | GTAAACAACC | 1920 |
| TTTTTGCATT | CTCATTCAAC | AAAAAAATCA | AAGAAGTGA | AGTCAAAAAA | GTCAAGCCC | 1980 |
| TCATAAGACA | TAAGTATAAA | GGGAAAGCTT | ATGAGATTCA | GCTTAGCTCT | GGTAGAAAAA | 2040 |
| TTAACATAAC | TGCTGGCCAT | AGTCTGTTTA | CAGTTAGAAA | TGGAGAAATA | AAGGAAGTTT | 2100 |
| CTGGAGATGG | GATAAAAGAA | GGTGACCTTA | TTGTAGCACC | AAAGAAAATT | AAACTCAATG | 2160 |
| AAAAAGGGGT | AAGCATAAAC | ATTCCCGAGT | TAATCTCAGA | TCTTTCCGAG | GAAGAAACAG | 2220 |

| | | | | | | |
|---|---|---|---|---|---|---|
| CCGACATTGT | GATGACGATT | TCAGCCAAGG | GCAGAAAGAA | CTTCTTTAAA | GGAATGCTGA | 2280 |
| GAACTTTAAG | GTGGATGTTT | GGAGAAGAAA | ATAGAAGGAT | AAGAACATTT | AATCGCTATT | 2340 |
| TGTTCCATCT | CGAAAAACTA | GGCCTTATCA | AACTACTGCC | CCGCGGATAT | GAAGTTACTG | 2400 |
| ACTGGGAGAG | ATTAAAGAAA | TATAAACAAC | TTTACGAGAA | GCTTGCTGGA | AGCGTTAAGT | 2460 |
| ACAACGGAAA | CAAGAGAGAG | TATTTAGTAA | TGTTCAACGA | GATCAAGGAT | TTTATATCTT | 2520 |
| ACTTCCCACA | AAAAGAGCTC | GAAGAATGGA | AAATTGGAAC | TCTCAATGGC | TTTAGAACGA | 2580 |
| ATTGTATTCT | CAAAGTCGAT | GAGGATTTTG | GAAGCTCCT | AGGTTACTAT | GTTAGTGAGG | 2640 |
| GCTATGCAGG | TGCACAAAAA | AATAAAACTG | GTGGTATCAG | TTATTCGGTG | AAGCTTTACA | 2700 |
| ATGAGGACCC | TAATGTTCTT | GAGAGCATGA | AAAATGTTGC | AGAAAAATTC | TTTGGCAAGG | 2760 |
| TTAGAGTTGA | CAGAAATTGC | GTAAGTATAT | CAAAGAAGAT | GGCATACTTA | GTTATGAAAT | 2820 |
| GCCTCTGTGG | AGCATTAGCC | GAAAACAAGA | GAATTCCTTC | TGTTATACTC | ACCTCTCCCG | 2880 |
| AACCGGTACG | GTGGTCATTT | TTAGAGGCGT | ATTTTACAGG | CGATGGAGAT | ATACATCCAT | 2940 |
| CAAAAAGGTT | TAGGCTCTCA | ACAAAAGCG | AGCTCCTTGC | AAATCAGCTT | GTGTTCTTGC | 3000 |
| TGAACTCTTT | GGGAATATCC | TCTGTAAAGA | TAGGCTTTGA | CAGTGGGGTC | TATAGAGTGT | 3060 |
| ATATAAATGA | AGACCTGCAA | TTTCCACAAA | CGTCTAGGGA | GAAAACACA | TACTACTCTA | 3120 |
| ACTTAATTCC | CAAAGAGATC | CTTAGGGACG | TGTTTGGAAA | AGAGTTCCAA | AGAACATGA | 3180 |
| CGTTCAAGAA | ATTTAAAGAG | CTTGTTGACT | CTGGAAAACT | TAACAGGGAG | AAAGCCAAGC | 3240 |
| TCTTGGAGTT | CTTCATTAAT | GGAGATATTG | TCCTTGACAG | AGTCAAAAGT | GTTAAAGAAA | 3300 |
| AGGACTATGA | AGGGTATGTC | TATGACCTAA | GCGTTGAGGA | TAACGAGAAC | TTTCTTGTTG | 3360 |
| GTTTTGGTTT | GCTCTATGCT | CACAACAGCT | ATTACGGCTA | TATGGGGTAT | CCTAAGGCAA | 3420 |
| GATGGTACTC | GAAGGAATGT | GCTGAAAGCG | TTACCGCATG | GGGGAGACAC | TACATAGAGA | 3480 |
| TGACGATAAG | AGAAATAGAG | GAAAAGTTCG | GCTTTAAGGT | TCTTTATGCG | GACAGTGTCT | 3540 |
| CAGGAGAAAG | TGAGATCATA | ATAAGGCAAA | ACGGAAAGAT | TAGATTTGTG | AAAATAAAGG | 3600 |
| ATCTTTTCTC | TAAGGTGGAC | TACAGCATTG | GCGAAAAAGA | ATACTGCATT | CTCGAAGGTG | 3660 |
| TTGAAGCACT | AACTCTGGAC | GATGACGGAA | AGCTTGTCTG | GAAGCCCGTC | CCCTACGTGA | 3720 |
| TGAGGCACAG | AGCGAATAAA | AGAATGTTCC | GCATCTGGCT | GACCAACAGC | TGGTATATAG | 3780 |
| ATGTTACTGA | GGATCATTCT | CTCATAGGCT | ATCTAAACAC | GTCAAAAACG | AAAACTGCCA | 3840 |
| AAAAAATCGG | GGAAAGACTA | AAGGAAGTAA | AGCCTTTTGA | ATTAGGCAAA | GCAGTAAAAT | 3900 |
| CGCTCATATG | CCCAAATGCA | CCGTTAAAGG | ATGAGAATAC | CAAAACTAGC | GAAATAGCAG | 3960 |
| TAAAATTCTG | GGAGCTCGTA | GGATTGATTG | TAGGAGATGG | AAACTGGGGT | GGAGATTCTC | 4020 |
| GTTGGGCAGA | GTATTATCTT | GGACTTTCAA | CAGGCAAAGA | TGCAGAAGAG | ATAAAGCAAA | 4080 |
| AACTTCTGGA | ACCCCTAAAA | ACTTATGGAG | TAATCTCAAA | CTATTACCCA | AAAAACGAGA | 4140 |
| AAGGGGACTT | CAACATCTTG | GCAAGAGCC | TTGTAAAGTT | TATGAAAAGG | CACTTTAAGG | 4200 |
| ACGAAAAAGG | AAGACGAAAA | ATTCCAGAGT | TCATGTATGA | GCTTCCGGTT | ACTTACATAG | 4260 |
| AGGCATTTCT | ACGAGGACTG | TTTTCAGCTG | ATGGTACTGT | AACTATCAGG | AAGGGAGTTC | 4320 |
| CAGAGATCAG | GCTAACAAAC | ATTGATGCTG | ACTTTCTAAG | GAAGTAAGG | AAGCTTCTGT | 4380 |
| GGATTGTTGG | AATTTCAAAT | TCAATATTTG | CTGAGACTAC | TCCAAATCGC | TACAATGGTG | 4440 |
| TTTCTACTGG | AACCTACTCA | AAGCATCTAA | GGATCAAAAA | TAAGTGGCGT | TTTGCTGAAA | 4500 |
| GGATAGGCTT | TTTAATCGAG | AGAAAGCAGA | AGAGACTTTT | AGAACATTTA | AAATCAGCGA | 4560 |
| GGGTAAAAAG | GAATACCATA | GATTTTGGCT | TTGATCTTGT | GCATGTGAAA | AAAGTCGAAG | 4620 |

-continued

| | | | | | |
|---|---|---|---|---|---|
| AGATACCATA | CGAGGGTTAC | GTTTATGACA | TTGAAGTCGA | AGAGACGCAT | AGGTTCTTTG | 4680 |
| CAAACAACAT | CCTGGTACAC | AATACTGACG | GCTTTTATGC | CACAATACCC | GGGGAAAAGC | 4740 |
| CTGAACTCAT | TAAAAGAAA | GCCAAGGAAT | TCCTAAACTA | CATAAACTCC | AAACTTCCAG | 4800 |
| GTCTGCTTGA | GCTTGAGTAT | GAGGGCTTTT | ACTTGAGAGG | ATTCTTTGTT | ACAAAAAGC | 4860 |
| GCTATGCAGT | CATAGATGAA | GAGGGCAGGA | TAACAACAAG | GGGCTTGGAA | GTAGTAAGGA | 4920 |
| GAGATTGGAG | TGAGATAGCT | AAGGAGACTC | AGGCAAGGT | TTTAGAGGCT | ATACTTAAAG | 4980 |
| AGGGAAGTGT | TGAAAAAGCT | GTAGAAGTTG | TTAGAGATGT | TGTAGAGAAA | ATAGCAAAAT | 5040 |
| ACAGGGTTCC | ACTTGAAAAG | CTTGTTATCC | ATGAGCAGAT | TACCAGGGAT | TTAAAGGACT | 5100 |
| ACAAAGCCAT | TGGCCCTCAT | GTCGCGATAG | CAAAAGACT | TGCCGCAAGA | GGGATAAAAG | 5160 |
| TGAAACCGGG | CACAATAATA | AGCTATATCG | TTCTCAAAGG | GAGCGGAAAG | ATAAGCGATA | 5220 |
| GGGTAATTTT | ACTTACAGAA | TACGATCCTA | GAAAACACAA | GTACGATCCG | GACTACTACA | 5280 |
| TAGAAAACCA | AGTTTGCCG | GCAGTACTTA | GGATACTCGA | AGCGTTTGGA | TACAGAAAGG | 5340 |
| AGGATTTAAG | GTATCAAAGC | TCAAAACAAA | CCGGCTTAGA | TGCATGGCTC | AAGAGGTAGC | 5400 |
| TCTGTTGCTT | TTTAGTCCAA | GTTTCTCCGC | GAGTCTCTCT | ATCTCTCTTT | TGTATTCTGC | 5460 |
| TATGTGGTTT | TCATTCACTA | TTAAGTAGTC | CGCCAAAGCC | ATAACGCTTC | CAATTCCAAA | 5520 |
| CTTGAGCTCT | TTCCAGTCTC | TGGCCTCAAA | TTCACTCCAT | GTTTTTGGAT | CGTCGCTTCT | 5580 |
| CCCTCTTCTG | CTAAGCCTCT | CGAATCTTTT | TCTTGGCGAA | GAGTGTACAG | CTATGATGAT | 5640 |
| TATCTCTTCC | TCTGGAAACG | CATCTTTAAA | CGTCTGAATT | TCATCTAGAG | ACCTCACTCC | 5700 |
| GTCGATTATA | ACTGCCTTGT | ACTTCTTTAG | TAGTTCTTTT | ACCTTTGGGA | TCGTTAATTT | 5760 |
| TGCCACGGCA | TTGTCCCCAA | GCTCCTGCCT | AAGCTGAATG | CTCACACTGT | TCATACCTTC | 5820 |
| GGGAGTTCTT | GGGATCC | | | | | 5837 |

( 2 ) INFORMATION FOR SEQ ID NO:2:

( i ) SEQUENCE CHARACTERISTICS:
        ( A ) LENGTH: 4707 base pairs
        ( B ) TYPE: nucleic acid
        ( C ) STRANDEDNESS: double
        ( D ) TOPOLOGY: Not Relevant ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 363..4296

( x i ) SEQUENCE DESCRIPTION: SEQ ID NO:2:

| | | | | | |
|---|---|---|---|---|---|
| GGATCCCTCT | CTTTTTGGTA | ACCCCATACG | TCATTCCCTC | AACCAAAACT | TCAGCATCGT | 60 |
| TGCAGTGGTC | AGTGTGTCTG | TGGGAGATGA | AGAGGACGTC | GATTTTCTG | GGGTCTATCT | 120 |
| TGTATCTCCA | CATTCTAACT | AACGCTCCAG | GCCCAGGATC | AACGTAGATG | TTTTTGCTCG | 180 |
| CCTTAATGAA | GAAGCCACCA | GTGGCTCTTG | CCTGCGTTAT | CGTGACGAAC | CTTCCACCAC | 240 |
| CGCCACCGAG | AAAAGTTATC | TCTATCATCT | CACACCTCCC | CCATAACATC | ACCTGCTCAA | 300 |
| TTTTTAAGCG | TTCTTAAAGG | CTTAAATACG | TGAATTTAGC | GTAAATTATT | GAGGGATTAA | 360 |

GT ATG ATA CTT GAC GCT GAC TAC ATC ACC GAG GAT GGG AAG CCG ATT     407
   Met Ile Leu Asp Ala Asp Tyr Ile Thr Glu Asp Gly Lys Pro Ile
    1          5               10             15

ATA AGG ATT TTC AAG AAA GAA AAC GGC GAG TTT AAG GTT GAG TAC GAC     455

|     |     |     |     |     |     |     |     |     |     |     |     |     |     |     |     |
|-----|-----|-----|-----|-----|-----|-----|-----|-----|-----|-----|-----|-----|-----|-----|-----|
| Ile | Arg | Ile | Phe | Lys | Lys | Glu | Asn | Gly | Glu | Phe | Lys | Val | Glu | Tyr | Asp |
|     |     |     |     | 20  |     |     |     |     | 25  |     |     |     |     | 30  |     |

| AGA | AAC | TTT | AGA | CCT | TAC | ATT | TAC | GCT | CTC | CTC | AAA | GAT | GAC | TCG | CAG | 503 |
|-----|-----|-----|-----|-----|-----|-----|-----|-----|-----|-----|-----|-----|-----|-----|-----|-----|
| Arg | Asn | Phe | Arg | Pro | Tyr | Ile | Tyr | Ala | Leu | Leu | Lys | Asp | Asp | Ser | Gln |     |
|     |     |     | 35  |     |     |     |     | 40  |     |     |     |     | 45  |     |     |     |

| ATT | GAT | GAG | GTT | AGG | AAG | ATA | ACC | GCC | GAG | AGG | CAT | GGG | AAG | ATA | GTG | 551 |
|-----|-----|-----|-----|-----|-----|-----|-----|-----|-----|-----|-----|-----|-----|-----|-----|-----|
| Ile | Asp | Glu | Val | Arg | Lys | Ile | Thr | Ala | Glu | Arg | His | Gly | Lys | Ile | Val |     |
|     |     | 50  |     |     |     |     | 55  |     |     |     |     | 60  |     |     |     |     |

| AGA | ATT | ATA | GAT | GCC | GAA | AAG | GTA | AGG | AAG | AAG | TTC | CTG | GGG | AGG | CCG | 599 |
|-----|-----|-----|-----|-----|-----|-----|-----|-----|-----|-----|-----|-----|-----|-----|-----|-----|
| Arg | Ile | Ile | Asp | Ala | Glu | Lys | Val | Arg | Lys | Lys | Phe | Leu | Gly | Arg | Pro |     |
|     | 65  |     |     |     |     | 70  |     |     |     |     | 75  |     |     |     |     |     |

| ATT | GAG | GTA | TGG | AGG | CTG | TAC | TTT | GAA | CAC | CCT | CAG | GAC | GTT | CCC | GCA | 647 |
|-----|-----|-----|-----|-----|-----|-----|-----|-----|-----|-----|-----|-----|-----|-----|-----|-----|
| Ile | Glu | Val | Trp | Arg | Leu | Tyr | Phe | Glu | His | Pro | Gln | Asp | Val | Pro | Ala |     |
| 80  |     |     |     |     | 85  |     |     |     |     | 90  |     |     |     |     | 95  |     |

| ATA | AGG | GAT | AAG | ATA | AGA | GAG | CAT | TCC | GCA | GTT | ATT | GAC | ATC | TTT | GAG | 695 |
|-----|-----|-----|-----|-----|-----|-----|-----|-----|-----|-----|-----|-----|-----|-----|-----|-----|
| Ile | Arg | Asp | Lys | Ile | Arg | Glu | His | Ser | Ala | Val | Ile | Asp | Ile | Phe | Glu |     |
|     |     |     |     | 100 |     |     |     |     | 105 |     |     |     |     | 110 |     |     |

| TAC | GAC | ATT | CCG | TTC | GCG | AAG | AGG | TAC | CTA | ATA | GAC | AAA | GGC | CTA | ATT | 743 |
|-----|-----|-----|-----|-----|-----|-----|-----|-----|-----|-----|-----|-----|-----|-----|-----|-----|
| Tyr | Asp | Ile | Pro | Phe | Ala | Lys | Arg | Tyr | Leu | Ile | Asp | Lys | Gly | Leu | Ile |     |
|     |     |     | 115 |     |     |     |     | 120 |     |     |     |     | 125 |     |     |     |

| CCA | ATG | GAA | GGC | GAT | GAA | GAG | CTC | AAG | TTG | CTC | GCA | TTT | GAC | ATA | GAA | 791 |
|-----|-----|-----|-----|-----|-----|-----|-----|-----|-----|-----|-----|-----|-----|-----|-----|-----|
| Pro | Met | Glu | Gly | Asp | Glu | Glu | Leu | Lys | Leu | Leu | Ala | Phe | Asp | Ile | Glu |     |
|     |     | 130 |     |     |     |     | 135 |     |     |     |     | 140 |     |     |     |     |

| ACC | CTC | TAT | CAC | GAA | GGG | GAG | GAG | TTC | GCG | AAG | GGG | CCC | ATT | ATA | ATG | 839 |
|-----|-----|-----|-----|-----|-----|-----|-----|-----|-----|-----|-----|-----|-----|-----|-----|-----|
| Thr | Leu | Tyr | His | Glu | Gly | Glu | Glu | Phe | Ala | Lys | Gly | Pro | Ile | Ile | Met |     |
|     |     | 145 |     |     |     |     | 150 |     |     |     |     | 155 |     |     |     |     |

| ATA | AGC | TAT | GCT | GAT | GAG | GAA | GAA | GCC | AAA | GTC | ATA | ACG | TGG | AAA | AAG | 887 |
|-----|-----|-----|-----|-----|-----|-----|-----|-----|-----|-----|-----|-----|-----|-----|-----|-----|
| Ile | Ser | Tyr | Ala | Asp | Glu | Glu | Glu | Ala | Lys | Val | Ile | Thr | Trp | Lys | Lys |     |
| 160 |     |     |     |     | 165 |     |     |     |     | 170 |     |     |     |     | 175 |     |

| ATC | GAT | CTC | CCG | TAC | GTC | GAG | GTA | GTT | TCC | AGC | GAG | AGG | GAG | ATG | ATA | 935 |
|-----|-----|-----|-----|-----|-----|-----|-----|-----|-----|-----|-----|-----|-----|-----|-----|-----|
| Ile | Asp | Leu | Pro | Tyr | Val | Glu | Val | Val | Ser | Ser | Glu | Arg | Glu | Met | Ile |     |
|     |     |     | 180 |     |     |     |     | 185 |     |     |     |     | 190 |     |     |     |

| AAG | CGG | TTC | CTC | AAG | GTG | ATA | AGG | GAG | AAA | GAT | CCC | GAT | GTT | ATA | ATT | 983 |
|-----|-----|-----|-----|-----|-----|-----|-----|-----|-----|-----|-----|-----|-----|-----|-----|-----|
| Lys | Arg | Phe | Leu | Lys | Val | Ile | Arg | Glu | Lys | Asp | Pro | Asp | Val | Ile | Ile |     |
|     |     |     | 195 |     |     |     |     | 200 |     |     |     |     | 205 |     |     |     |

| ACC | TAC | AAC | GGC | GAT | TCT | TTC | GAC | CTT | CCC | TAT | CTA | GTT | AAG | AGG | GCC | 1031 |
|-----|-----|-----|-----|-----|-----|-----|-----|-----|-----|-----|-----|-----|-----|-----|-----|------|
| Thr | Tyr | Asn | Gly | Asp | Ser | Phe | Asp | Leu | Pro | Tyr | Leu | Val | Lys | Arg | Ala |      |
|     |     | 210 |     |     |     |     | 215 |     |     |     |     | 220 |     |     |     |      |

| GAA | AAG | CTC | GGG | ATA | AAG | CTA | CCC | CTG | GGA | AGG | GAC | GGT | AGT | GAG | CCA | 1079 |
|-----|-----|-----|-----|-----|-----|-----|-----|-----|-----|-----|-----|-----|-----|-----|-----|------|
| Glu | Lys | Leu | Gly | Ile | Lys | Leu | Pro | Leu | Gly | Arg | Asp | Gly | Ser | Glu | Pro |      |
|     | 225 |     |     |     |     | 230 |     |     |     |     | 235 |     |     |     |     |      |

| AAG | ATG | CAG | AGG | CTT | GGG | GAT | ATG | ACA | GCG | GTG | GAG | ATA | AAG | GGA | AGG | 1127 |
|-----|-----|-----|-----|-----|-----|-----|-----|-----|-----|-----|-----|-----|-----|-----|-----|------|
| Lys | Met | Gln | Arg | Leu | Gly | Asp | Met | Thr | Ala | Val | Glu | Ile | Lys | Gly | Arg |      |
| 240 |     |     |     |     | 245 |     |     |     |     | 250 |     |     |     |     | 255 |      |

| ATA | CAC | TTT | GAC | CTC | TAC | CAC | GTG | ATT | AGG | AGA | ACG | ATA | AAC | CTC | CCA | 1175 |
|-----|-----|-----|-----|-----|-----|-----|-----|-----|-----|-----|-----|-----|-----|-----|-----|------|
| Ile | His | Phe | Asp | Leu | Tyr | His | Val | Ile | Arg | Arg | Thr | Ile | Asn | Leu | Pro |      |
|     |     |     |     | 260 |     |     |     |     | 265 |     |     |     |     | 270 |     |      |

| ACA | TAC | ACC | CTC | GAG | GCA | GTT | TAT | GAG | GCA | ATC | TTC | GGA | AAG | CCA | AAG | 1223 |
|-----|-----|-----|-----|-----|-----|-----|-----|-----|-----|-----|-----|-----|-----|-----|-----|------|
| Thr | Tyr | Thr | Leu | Glu | Ala | Val | Tyr | Glu | Ala | Ile | Phe | Gly | Lys | Pro | Lys |      |
|     |     |     | 275 |     |     |     |     | 280 |     |     |     |     | 285 |     |     |      |

| GAG | AAA | GTT | TAC | GCT | CAC | GAG | ATA | GCT | GAG | GCC | TGG | GAG | ACT | GGA | AAG | 1271 |
|-----|-----|-----|-----|-----|-----|-----|-----|-----|-----|-----|-----|-----|-----|-----|-----|------|
| Glu | Lys | Val | Tyr | Ala | His | Glu | Ile | Ala | Glu | Ala | Trp | Glu | Thr | Gly | Lys |      |
|     |     | 290 |     |     |     |     | 295 |     |     |     |     | 300 |     |     |     |      |

| GGA | CTG | GAG | AGA | GTT | GCA | AAG | TAT | TCA | ATG | GAG | GAT | GCA | AAG | GTA | ACG | 1319 |
|-----|-----|-----|-----|-----|-----|-----|-----|-----|-----|-----|-----|-----|-----|-----|-----|------|
| Gly | Leu | Glu | Arg | Val | Ala | Lys | Tyr | Ser | Met | Glu | Asp | Ala | Lys | Val | Thr |      |
|     | 305 |     |     |     |     | 310 |     |     |     |     | 315 |     |     |     |     |      |

| TAC | GAG | CTC | GGT | AGG | GAG | TTC | TTC | CCA | ATG | GAG | GCC | CAG | CTT | TCA | AGG | 1367 |
|-----|-----|-----|-----|-----|-----|-----|-----|-----|-----|-----|-----|-----|-----|-----|-----|------|
| Tyr | Glu | Leu | Gly | Arg | Glu | Phe | Phe | Pro | Met | Glu | Ala | Gln | Leu | Ser | Arg |      |
| 320 |     |     |     |     | 325 |     |     |     |     | 330 |     |     |     |     | 335 |      |

| TTA | GTC | GGC | CAG | CCC | CTG | TGG | GAT | GTT | TCT | AGG | TCT | TCA | ACT | GGC | AAC | 1415 |

```
                Leu Val Gly Gln Pro Leu Trp Asp Val Ser Arg Ser Ser Thr Gly Asn
                                340             345                 350

TTG GTG GAG TGG TAC CTC CTC AGG AAG GCC TAC GAG AGG AAT GAA TTG             1463
Leu Val Glu Trp Tyr Leu Leu Arg Lys Ala Tyr Glu Arg Asn Glu Leu
            355                 360                 365

GCT CCA AAC AAG CCG GAT GAG AGG GAG TAC GAG AGA AGG CTA AGG GAG             1511
Ala Pro Asn Lys Pro Asp Glu Arg Glu Tyr Glu Arg Arg Leu Arg Glu
        370                 375                 380

AGC TAC GCT GGG GGA TAC GTT AAG GAG CCG GAG AAA GGG CTC TGG GAG             1559
Ser Tyr Ala Gly Gly Tyr Val Lys Glu Pro Glu Lys Gly Leu Trp Glu
    385                 390                 395

GGG TTA GTT TCC CTA GAT TTC AGG AGC CTG TAC CCC TCG ATA ATA ATC             1607
Gly Leu Val Ser Leu Asp Phe Arg Ser Leu Tyr Pro Ser Ile Ile Ile
400                 405                 410                 415

ACC CAT AAC GTC TCA CCG GAT ACG CTG AAC AGG GAA GGG TGT AGG GAA             1655
Thr His Asn Val Ser Pro Asp Thr Leu Asn Arg Glu Gly Cys Arg Glu
                420                 425                 430

TAC GAT GTC GCC CCA GAG GTT GGG CAC AAG TTC TGC AAG GAC TTC CCG             1703
Tyr Asp Val Ala Pro Glu Val Gly His Lys Phe Cys Lys Asp Phe Pro
            435                 440                 445

GGG TTT ATC CCC AGC CTG CTC AAG AGG TTA TTG GAT GAA AGG CAA GAA             1751
Gly Phe Ile Pro Ser Leu Leu Lys Arg Leu Leu Asp Glu Arg Gln Glu
        450                 455                 460

ATA AAA AGG AAG ATG AAA GCT TCT AAA GAC CCA ATC GAG AAG AAG ATG             1799
Ile Lys Arg Lys Met Lys Ala Ser Lys Asp Pro Ile Glu Lys Lys Met
    465                 470                 475

CTT GAT TAC AGG CAA CGG GCA ATC AAA ATC CTG GCA AAC AGC ATT TTA             1847
Leu Asp Tyr Arg Gln Arg Ala Ile Lys Ile Leu Ala Asn Ser Ile Leu
480                 485                 490                 495

CCG GAA GAA TGG GTT CCA CTA ATT AAA AAC GGT AAA GTT AAG ATA TTC             1895
Pro Glu Glu Trp Val Pro Leu Ile Lys Asn Gly Lys Val Lys Ile Phe
                500                 505                 510

CGC ATT GGG GAC TTC GTT GAT GGA CTT ATG AAG GCG AAC CAA GGA AAA             1943
Arg Ile Gly Asp Phe Val Asp Gly Leu Met Lys Ala Asn Gln Gly Lys
            515                 520                 525

GTG AAG AAA ACG GGG GAT ACA GAA GTT TTA GAA GTT GCA GGA ATT CAT             1991
Val Lys Lys Thr Gly Asp Thr Glu Val Leu Glu Val Ala Gly Ile His
        530                 535                 540

GCG TTT TCC TTT GAC AGG AAG TCC AAG AAG GCC CGT GTA ATG GCA GTG             2039
Ala Phe Ser Phe Asp Arg Lys Ser Lys Lys Ala Arg Val Met Ala Val
    545                 550                 555

AAA GCC GTG ATA AGA CAC CGT TAT TCC GGA AAT GTT TAT AGA ATA GTC             2087
Lys Ala Val Ile Arg His Arg Tyr Ser Gly Asn Val Tyr Arg Ile Val
560                 565                 570                 575

TTA AAC TCT GGT AGA AAA ATA ACA ATA ACA GAA GGG CAT AGC CTA TTT             2135
Leu Asn Ser Gly Arg Lys Ile Thr Ile Thr Glu Gly His Ser Leu Phe
                580                 585                 590

GTC TAT AGG AAC GGG GAT CTC GTT GAG GCA ACT GGG GAG GAT GTC AAA             2183
Val Tyr Arg Asn Gly Asp Leu Val Glu Ala Thr Gly Glu Asp Val Lys
            595                 600                 605

ATT GGG GAT CTT CTT GCA GTT CCA AGA TCA GTA AAC CTA CCA GAG AAA             2231
Ile Gly Asp Leu Leu Ala Val Pro Arg Ser Val Asn Leu Pro Glu Lys
        610                 615                 620

AGG GAA CGC TTG AAT ATT GTT GAA CTT CTT CTG AAT CTC TCA CCG GAA             2279
Arg Glu Arg Leu Asn Ile Val Glu Leu Leu Leu Asn Leu Ser Pro Glu
    625                 630                 635

GAG ACA GAA GAT ATA ATA CTT ACG ATT CCA GTT AAA GGC AGA AAG AAC             2327
Glu Thr Glu Asp Ile Ile Leu Thr Ile Pro Val Lys Gly Arg Lys Asn
640                 645                 650                 655

TTC TTC AAG GGA ATG TTG AGA ACA TTA CGT TGG ATT TTT GGT GAG GAA             2375
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Phe | Phe | Lys | Gly | Met | Leu | Arg | Thr | Leu | Arg | Trp | Ile | Phe | Gly | Glu | Glu |      |
|     |     |     |     | 660 |     |     |     |     | 665 |     |     |     |     | 670 |     |      |
| AAG | AGA | GTA | AGG | ACA | GCG | AGC | CGC | TAT | CTA | AGA | CAC | CTT | GAA | AAT | CTC | 2423 |
| Lys | Arg | Val | Arg | Thr | Ala | Ser | Arg | Tyr | Leu | Arg | His | Leu | Glu | Asn | Leu |      |
|     |     |     | 675 |     |     |     | 680 |     |     |     |     | 685 |     |     |     |      |
| GGA | TAC | ATA | AGG | TTG | AGG | AAA | ATT | GGA | TAC | GAC | ATC | ATT | GAT | AAG | GAG | 2471 |
| Gly | Tyr | Ile | Arg | Leu | Arg | Lys | Ile | Gly | Tyr | Asp | Ile | Ile | Asp | Lys | Glu |      |
|     |     | 690 |     |     |     | 695 |     |     |     |     | 700 |     |     |     |     |      |
| GGG | CTT | GAG | AAA | TAT | AGA | ACG | TTG | TAC | GAG | AAA | CTT | GTT | GAT | GTT | GTC | 2519 |
| Gly | Leu | Glu | Lys | Tyr | Arg | Thr | Leu | Tyr | Glu | Lys | Leu | Val | Asp | Val | Val |      |
|     | 705 |     |     |     | 710 |     |     |     |     | 715 |     |     |     |     |     |      |
| CGC | TAT | AAT | GGC | AAC | AAG | AGA | GAG | TAT | TTA | GTT | GAA | TTT | AAT | GCT | GTC | 2567 |
| Arg | Tyr | Asn | Gly | Asn | Lys | Arg | Glu | Tyr | Leu | Val | Glu | Phe | Asn | Ala | Val |      |
| 720 |     |     |     | 725 |     |     |     | 730 |     |     |     |     | 735 |     |     |      |
| CGG | GAC | GTT | ATC | TCA | CTA | ATG | CCA | GAG | GAA | GAA | CTG | AAG | GAA | TGG | CGT | 2615 |
| Arg | Asp | Val | Ile | Ser | Leu | Met | Pro | Glu | Glu | Glu | Leu | Lys | Glu | Trp | Arg |      |
|     |     |     |     | 740 |     |     |     | 745 |     |     |     | 750 |     |     |     |      |
| ATT | GGA | ACT | AGA | AAT | GGA | TTC | AGA | ATG | GGT | ACG | TTC | GTA | GAT | ATT | GAT | 2663 |
| Ile | Gly | Thr | Arg | Asn | Gly | Phe | Arg | Met | Gly | Thr | Phe | Val | Asp | Ile | Asp |      |
|     |     |     | 755 |     |     |     | 760 |     |     |     |     | 765 |     |     |     |      |
| GAA | GAT | TTT | GCC | AAG | CTT | CTT | GGC | TAC | TAT | GTG | AGC | GAG | GGA | AGT | GCG | 2711 |
| Glu | Asp | Phe | Ala | Lys | Leu | Leu | Gly | Tyr | Tyr | Val | Ser | Glu | Gly | Ser | Ala |      |
|     |     | 770 |     |     |     | 775 |     |     |     |     | 780 |     |     |     |     |      |
| AGG | AAG | TGG | AAG | AAT | CAA | ACT | GGA | GGT | TGG | AGT | TAC | ACT | GTG | AGA | TTG | 2759 |
| Arg | Lys | Trp | Lys | Asn | Gln | Thr | Gly | Gly | Trp | Ser | Tyr | Thr | Val | Arg | Leu |      |
|     | 785 |     |     |     | 790 |     |     |     |     | 795 |     |     |     |     |     |      |
| TAC | AAC | GAG | AAC | GAT | GAA | GTT | CTT | GAC | GAC | ATG | GAA | CAC | TTA | GCC | AAG | 2807 |
| Tyr | Asn | Glu | Asn | Asp | Glu | Val | Leu | Asp | Asp | Met | Glu | His | Leu | Ala | Lys |      |
| 800 |     |     |     | 805 |     |     |     | 810 |     |     |     |     | 815 |     |     |      |
| AAG | TTT | TTT | GGG | AAA | GTC | AAA | CGT | GGA | AAG | AAC | TAT | GTT | GAG | ATA | CCA | 2855 |
| Lys | Phe | Phe | Gly | Lys | Val | Lys | Arg | Gly | Lys | Asn | Tyr | Val | Glu | Ile | Pro |      |
|     |     |     |     | 820 |     |     |     | 825 |     |     |     |     | 830 |     |     |      |
| AAG | AAA | ATG | GCT | TAT | ATC | ATC | TTT | GAG | AGC | CTT | TGT | GGG | ACT | TTG | GCA | 2903 |
| Lys | Lys | Met | Ala | Tyr | Ile | Ile | Phe | Glu | Ser | Leu | Cys | Gly | Thr | Leu | Ala |      |
|     |     |     | 835 |     |     |     |     | 840 |     |     |     |     | 845 |     |     |      |
| GAA | AAC | AAA | AGG | GTT | CCT | GAG | GTA | ATC | TTT | ACC | TCA | TCA | AAG | GGC | GTT | 2951 |
| Glu | Asn | Lys | Arg | Val | Pro | Glu | Val | Ile | Phe | Thr | Ser | Ser | Lys | Gly | Val |      |
|     |     | 850 |     |     |     |     | 855 |     |     |     |     | 860 |     |     |     |      |
| AGA | TGG | GCC | TTC | CTT | GAG | GGT | TAT | TTC | ATC | GGC | GAT | GGC | GAT | GTT | CAC | 2999 |
| Arg | Trp | Ala | Phe | Leu | Glu | Gly | Tyr | Phe | Ile | Gly | Asp | Gly | Asp | Val | His |      |
|     | 865 |     |     |     |     | 870 |     |     |     |     | 875 |     |     |     |     |      |
| CCA | AGC | AAG | AGG | GTT | CGC | CTA | TCA | ACG | AAG | AGC | GAG | CTT | TTA | GTA | AAT | 3047 |
| Pro | Ser | Lys | Arg | Val | Arg | Leu | Ser | Thr | Lys | Ser | Glu | Leu | Leu | Val | Asn |      |
| 880 |     |     |     |     | 885 |     |     |     |     | 890 |     |     |     |     | 895 |      |
| GGC | CTT | GTT | CTC | CTA | CTT | AAC | TCC | CTT | GGA | GTA | TCT | GCC | ATT | AAG | CTT | 3095 |
| Gly | Leu | Val | Leu | Leu | Leu | Asn | Ser | Leu | Gly | Val | Ser | Ala | Ile | Lys | Leu |      |
|     |     |     |     | 900 |     |     |     |     | 905 |     |     |     |     | 910 |     |      |
| GGA | TAC | GAT | AGC | GGA | GTC | TAC | AGG | GTT | TAT | GTA | AAC | GAG | GAA | CTT | AAG | 3143 |
| Gly | Tyr | Asp | Ser | Gly | Val | Tyr | Arg | Val | Tyr | Val | Asn | Glu | Glu | Leu | Lys |      |
|     |     |     | 915 |     |     |     | 920 |     |     |     |     | 925 |     |     |     |      |
| TTT | ACG | GAA | TAC | AGA | AAG | AAA | AAG | AAT | GTA | TAT | CAC | TCT | CAC | ATT | GTT | 3191 |
| Phe | Thr | Glu | Tyr | Arg | Lys | Lys | Lys | Asn | Val | Tyr | His | Ser | His | Ile | Val |      |
|     |     | 930 |     |     |     | 935 |     |     |     |     | 940 |     |     |     |     |      |
| CCA | AAG | GAT | ATT | CTC | AAA | GAA | ACT | TTT | GGT | AAG | GTC | TTC | CAG | AAA | AAT | 3239 |
| Pro | Lys | Asp | Ile | Leu | Lys | Glu | Thr | Phe | Gly | Lys | Val | Phe | Gln | Lys | Asn |      |
|     | 945 |     |     |     | 950 |     |     |     |     | 955 |     |     |     |     |     |      |
| ATA | AGT | TAC | AAG | AAA | TTT | AGA | GAG | CTT | GTA | GAA | AAT | GGA | AAA | CTT | GAC | 3287 |
| Ile | Ser | Tyr | Lys | Lys | Phe | Arg | Glu | Leu | Val | Glu | Asn | Gly | Lys | Leu | Asp |      |
| 960 |     |     |     |     | 965 |     |     |     |     | 970 |     |     |     |     | 975 |      |
| AGG | GAG | AAA | GCC | AAA | CGC | ATT | GAG | TGG | TTA | CTT | AAC | GGA | GAT | ATA | GTC | 3335 |

```
                Arg Glu Lys Ala Lys Arg Ile Glu Trp Leu Leu Asn Gly Asp Ile Val
                            980                 985                 990

CTA GAT AGA GTC GTA GAG ATT AAG AGA GAG TAC TAT GAT GGT TAC GTT              3383
Leu Asp Arg Val Val Glu Ile Lys Arg Glu Tyr Tyr Asp Gly Tyr Val
            995                 1000                1005

TAC GAT CTA AGT GTC GAT GAA GAT GAG AAT TTC CTT GCT GGC TTT GGA              3431
Tyr Asp Leu Ser Val Asp Glu Asp Glu Asn Phe Leu Ala Gly Phe Gly
            1010                1015                1020

TTC CTC TAT GCA CAT AAT AGC TAT TAT GGG TAT TAT GGG TAC GCA AAA              3479
Phe Leu Tyr Ala His Asn Ser Tyr Tyr Gly Tyr Tyr Gly Tyr Ala Lys
        1025                1030                1035

GCC CGT TGG TAC TGT AAG GAG TGC GCA GAG AGC GTT ACG GCC TGG GGG              3527
Ala Arg Trp Tyr Cys Lys Glu Cys Ala Glu Ser Val Thr Ala Trp Gly
1040                1045                1050                1055

AGG GAA TAT ATA GAG TTC GTA AGG AAG GAA CTG GAG GAA AAG TTC GGG              3575
Arg Glu Tyr Ile Glu Phe Val Arg Lys Glu Leu Glu Glu Lys Phe Gly
                1060                1065                1070

TTC AAA GTC TTA TAC ATA GAC ACA GAT GGA CTC TAC GCC ACA ATT CCT              3623
Phe Lys Val Leu Tyr Ile Asp Thr Asp Gly Leu Tyr Ala Thr Ile Pro
            1075                1080                1085

GGG GCA AAA CCC GAG GAG ATA AAG AAG AAA GCC CTA GAG TTC GTA GAT              3671
Gly Ala Lys Pro Glu Glu Ile Lys Lys Lys Ala Leu Glu Phe Val Asp
        1090                1095                1100

TAT ATA AAC GCC AAG CTC CCA GGG CTG TTG GAG CTT GAG TAC GAG GGC              3719
Tyr Ile Asn Ala Lys Leu Pro Gly Leu Leu Glu Leu Glu Tyr Glu Gly
        1105                1110                1115

TTC TAC GTG AGA GGG TTC TTC GTG ACG AAG AAG AAG TAT GCG TTG ATA              3767
Phe Tyr Val Arg Gly Phe Phe Val Thr Lys Lys Lys Tyr Ala Leu Ile
1120                1125                1130                1135

GAT GAG GAA GGG AAG ATA ATC ACT AGG GGG CTT GAA ATA GTC AGG AGG              3815
Asp Glu Glu Gly Lys Ile Ile Thr Arg Gly Leu Glu Ile Val Arg Arg
                1140                1145                1150

GAC TGG AGC GAA ATA GCC AAA GAA ACC CAA GCA AAA GTC CTA GAG GCT              3863
Asp Trp Ser Glu Ile Ala Lys Glu Thr Gln Ala Lys Val Leu Glu Ala
            1155                1160                1165

ATC CTA AAG CAT GGC AAC GTT GAG GAG GCA GTA AAG ATA GTT AAG GAG              3911
Ile Leu Lys His Gly Asn Val Glu Glu Ala Val Lys Ile Val Lys Glu
        1170                1175                1180

GTA ACT GAA AAG CTG AGC AAG TAC GAA ATA CCT CCA GAA AAG CTA GTT              3959
Val Thr Glu Lys Leu Ser Lys Tyr Glu Ile Pro Pro Glu Lys Leu Val
        1185                1190                1195

ATT TAC GAG CAG ATC ACG AGG CCC CTT CAC GAG TAC AAG GCT ATA GGT              4007
Ile Tyr Glu Gln Ile Thr Arg Pro Leu His Glu Tyr Lys Ala Ile Gly
1200                1205                1210                1215

CCG CAC GTT GCC GTG GCA AAA AGG TTA GCC GCT AGA GGA GTA AAG GTG              4055
Pro His Val Ala Val Ala Lys Arg Leu Ala Ala Arg Gly Val Lys Val
            1220                1225                1230

AGG CCT GGC ATG GTG ATA GGG TAC ATA GTG CTG AGG GGA GAC GGG CCA              4103
Arg Pro Gly Met Val Ile Gly Tyr Ile Val Leu Arg Gly Asp Gly Pro
            1235                1240                1245

ATA AGC AAG AGG GCT ATC CTT GCA GAG GAG TTC GAT CTC AGG AAG CAT              4151
Ile Ser Lys Arg Ala Ile Leu Ala Glu Glu Phe Asp Leu Arg Lys His
        1250                1255                1260

AAG TAT GAC GCT GAG TAT TAC ATA GAA AAT CAG GTT TTA CCT GCC GTT              4199
Lys Tyr Asp Ala Glu Tyr Tyr Ile Glu Asn Gln Val Leu Pro Ala Val
        1265                1270                1275

CTT AGA ATA TTA GAG GCC TTT GGG TAC AGG AAA GAA GAC CTC AGG TGG              4247
Leu Arg Ile Leu Glu Ala Phe Gly Tyr Arg Lys Glu Asp Leu Arg Trp
        1280                1285                1290                1295

CAG AAG ACT AAA CAG ACA GGT CTT ACG GCA TGG CTT AAC ATC AAG AAG A        4296
```

```
Gln Lys Thr Lys Gln Thr Gly Leu Thr Ala Trp Leu Asn Ile Lys Lys
            1300                1305                1310
```

| | | | | | |
|---|---|---|---|---|---|
| AGTAATGTTT | ATGTACTCGT | AATGCGAGTA | TTAAGTGGGT | GATGAGATGG | CAGTATTGAG | 4356 |
| CATAAGGATT | CCGGATGATC | TAAAAGAGAA | GATGAAGGAG | TTTGACATAA | ACTGGAGTGA | 4416 |
| GGAGATCAGG | AAGTTCATAA | AAGAGAGGAT | AGAGTATGAG | GAAAGGAAGA | GAACCCTTGA | 4476 |
| GAAAGCTCTA | GAACTTCTAA | AGAATACTCC | AGGATCAGTC | GAGAGAGGAT | TTTCAGCAAG | 4536 |
| GGCAGTGAGG | GAGGATCGTG | ATAGTCATTG | ATGCATCAAT | CCTAGCTAAA | ATAATTCTAA | 4596 |
| AAGAAGAGGG | CTGGGAACAG | ATAACTCTTA | CACCGAGCAC | GATAACTTTG | GACTATGCTT | 4656 |
| TTGTTGAATG | TACAAACGCA | ATATGGAAGG | CTGTCAGGCG | GAACAGGATC | C | 4707 |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGTGTCTCCG GAGAAAGTGA GAT        23

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGTATTGTGT ACCAGGATGT TG        22

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AGCATTTTAC CGGAAGAATG GGTT        24

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GCTATTATGT GCATAGAGGA ATCCA        25

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AGGGTCGACA GATTTGATCC AGCG  24

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GAGAACTTTG TTCGTACCTG  20

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GGTATTATTT CTTCTAAAGC A  21

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GTTGTTTGTT GGTTTTACCA  20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ATGGCAAATG CTGTATGGAT  20

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AGTGTCTCCG GAGAAAGTGA GAT  23

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATTGTGTACT AGTATGTTGT TTGCAA  26

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GCCTCCGGAG ACACTATCGC CAAAATCACC GCCGTAA 37

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GCCACTAGTA CACAATACGC CGAACGATCG CCAGTTCT 38

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCTTCTAGAC CGGTGCAGTA TGAAGG 26

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GCCGTCGACC CTAGTGTCTC AGGAGAAAGT GAGATC 36

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GCCTCTAGAA TTGTGTACCA GGATGTTGTT TGC 33

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GCAAAGAACC GGTGCGTCTC TTC 23

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

AGCAACAGAG TTACCTCTTG 20

( 2 ) INFORMATION FOR SEQ ID NO:21:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

CAGTTTCCAG CTCCTACAAT GAGACCTACG AGC 33

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

GTAGTGTCGA CCCCATGCGG 20

( 2 ) INFORMATION FOR SEQ ID NO:23:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

CGTTTTGCCT GATTATTATC TCACTTTC 28

( 2 ) INFORMATION FOR SEQ ID NO:24:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

GTCCACCTTC GAAAAAGAT CC 22

( 2 ) INFORMATION FOR SEQ ID NO:25:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

CCGCATAAAG GACCTTAAAG C 21

( 2 ) INFORMATION FOR SEQ ID NO:26:

( i ) SEQUENCE CHARACTERISTICS:

(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:26:

GAGGAAGAGA TCATCATCAT AGC  23

(2) INFORMATION FOR SEQ ID NO:27:

(i) SEQUENCE CHARACTERISTICS:
(A) LENGTH: 40 base pairs
(B) TYPE: nucleic acid
(C) STRANDEDNESS: double
(D) TOPOLOGY: linear (xi) SEQUENCE DESCRIPTION: SEQ ID NO:27:

GTCCTTCGTG CGGACAGTGT CTCAGGAGAA AGTGAGATAA  40

(2) INFORMATION FOR SEQ ID NO:28:

(i) SEQUENCE CHARACTERISTICS:
(A) LENGTH: 40 base pairs
(B) TYPE: nucleic acid
(C) STRANDEDNESS: double
(D) TOPOLOGY: linear (xi) SEQUENCE DESCRIPTION: SEQ ID NO:28:

GTCCTTTATG CGGACTAGGT CTCAGGAGAA AGTGAGATAA  40

(2) INFORMATION FOR SEQ ID NO:29:

(i) SEQUENCE CHARACTERISTICS:
(A) LENGTH: 61 base pairs
(B) TYPE: nucleic acid
(C) STRANDEDNESS: double
(D) TOPOLOGY: linear (xi) SEQUENCE DESCRIPTION: SEQ ID NO:29:

CCGGTTCTTT GCAAACAACA TCCTGGTACA CAATTAAGAC GGCTTTTATG CCACAATACC  60
C  61

(2) INFORMATION FOR SEQ ID NO:30:

(i) SEQUENCE CHARACTERISTICS:
(A) LENGTH: 22 amino acids
(B) TYPE: amino acid
(C) STRANDEDNESS: unknown
(D) TOPOLOGY: unknown (xi) SEQUENCE DESCRIPTION: SEQ ID NO:30:

Ile Lys Ile Leu Ala Asn Ser Ile Leu Pro Glu Glu Trp Val Pro Leu
1               5                   10                  15
Ile Lys Asn Gly Lys Val
            20

(2) INFORMATION FOR SEQ ID NO:31:

(i) SEQUENCE CHARACTERISTICS:
(A) LENGTH: 22 amino acids
(B) TYPE: amino acid
(C) STRANDEDNESS: unknown
(D) TOPOLOGY: unknown (xi) SEQUENCE DESCRIPTION: SEQ ID NO:31:

Ile Lys Leu Leu Ala Asn Ser Ile Leu Pro Asn Glu Trp Leu Pro
1               5                   10                  15

Ile Ile Glu Asn Gly Glu Ile
1                   20

(2) INFORMATION FOR SEQ ID NO:32:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (xi) SEQUENCE DESCRIPTION: SEQ ID NO:32:

Lys Val Leu Tyr Ala Asp Ser Val Ser Gly Glu Ser Glu Ile Ile Ile
1               5                   10                  15

Arg Gln Asn Gly Lys Ile
            20

(2) INFORMATION FOR SEQ ID NO:33:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (xi) SEQUENCE DESCRIPTION: SEQ ID NO:33:

Ala Ile Leu Tyr Val Gly Cys Gly Ala Lys Gly Thr Asn Val Leu Met
1               5                   10                  15

Ala Asp Gly Ser Ile Glu
            20

(2) INFORMATION FOR SEQ ID NO:34:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (xi) SEQUENCE DESCRIPTION: SEQ ID NO:34:

Lys Val Val Lys Asn Lys Cys Leu Ala Glu Gly Thr Arg Ile Arg Asp
1               5                   10                  15

Pro Val Thr Gly Thr Thr
            20

(2) INFORMATION FOR SEQ ID NO:35:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (xi) SEQUENCE DESCRIPTION: SEQ ID NO:35:

Glu Asx Gly Lys Ala Gly Phe Gly Phe Leu Tyr Ala His Asn Ser Tyr
1               5                   10                  15

Tyr Gly Tyr Tyr Gly Tyr Ala
            20

(2) INFORMATION FOR SEQ ID NO:36:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown 5,496,714

47                                                           48
-continued ( x i ) SEQUENCE DESCRIPTION: SEQ ID NO:36:

Glu  Asn  Phe  Leu  Val  Gly  Phe  Gly  Leu  Leu  Tyr  Ala  His  Asn  Ser  Tyr
1                  5                           10                          15

Tyr  Gly  Tyr  Met  Gly  Tyr  Pro
               20

( 2 ) INFORMATION FOR SEQ ID NO:37:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:37:

Glu  Thr  His  Arg  Phe  Phe  Ala  Asn  Asn  Ile  Leu  Val  His  Asn  Thr  Asp
1                  5                           10                          15

Gly  Phe  Tyr  Ala  Thr  Ile  Pro
               20

( 2 ) INFORMATION FOR SEQ ID NO:38:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:38:

Asp  His  Gln  Phe  Leu  Leu  Ala  Asn  Gln  Val  Val  Val  His  Asn  Cys  Gly
1                  5                           10                          15

Glu  Arg  Gly  Asn  Glu  Met  Ala
               20

( 2 ) INFORMATION FOR SEQ ID NO:39:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:39:

Glu  Leu  His  Thr  Leu  Val  Ala  Glu  Gly  Val  Val  Val  His  Asn  Cys  Ser
1                  5                           10                          15

Pro  Pro  Phe  Lys  Gln  Ala  Glu
               20

MODIFICATION OF PROTEIN BY USE OF A CONTROLLABLE INTERVEINING PROTEIN SEQUENCE

BACKGROUND OF THE INVENTION

The present invention is directed to modified proteins and methods of producing the same. More specifically, the modified protein of the present invention is a target protein into which is inserted a controllable intervening protein sequence (CIVPS), the CIVPS being capable of excision under predetermined conditions.

Production of mature proteins involves the flow of information from DNA to RNA to protein. Precise excision of DNA and RNA elements which interrupt that information has been previously described [M. Belfort, *Annu. Rev. Genet.* 24, 363 (1990); T. R. Cech, *Annu. Rev. Biochem.* 59, 543 (1990); Hunter et al., *Genes Dev.* 3, 2101 (1989)]. More recently, evidence for the precise excision of intervening protein sequences has also been described for the TFPI allele from *Saccharomyces cerevisiae* [Hirata et al., *J. Biol. Chem.* 265, 6726 (1990); Kane et al., Science 250, 651 (1990)] and the rec A gene from *Mycobacterium tuberculosis* [Davis et al., *J. Bact.* 173, 5653 (1991); Davis et al., *Cell* 71:1 (1992)]. Each contains internal in-frame peptide segments which must be removed to produce the mature protein. Expression of Tfp1 and Rec A each results in two peptides: one representing the intervening protein sequence (IVPS) and the other the ligated product of the external protein sequences (EPS). This post-translational processing event has been termed "protein splicing". Similarly, the Vent DNA polymerase gene from the hyperthermophilic archaea *Thermococcus litoralis* contains two in-frame IVPSs [Perler, et al., PNAS 89, 5577 (1992)].

A major impediment to the development of methods of using IVPSs or protein splicing in other than research applications has been the inability to control the activity of the IVPS and thus the splicing event.

Thus, it would be desirable to have a method which provides a ready means to modify a target protein using an IVPS, particularly where the activity of the IVPS is controllable. It would also be desirable to have a method which can specifically modify target proteins such that their activity is substantially inactivated. It would be desirable to have a method which can be used to restore the activity of an inactivated modified protein.

SUMMARY OF THE INVENTION

The present invention relates to modified proteins comprising an IVPS inserted into a target protein, the IVPS being capable of excision by protein splicing under predetermined conditions. Such predetermined conditions depend on the IVPS used and can include, for example, increase in temperature, exposure to light, dephosphorylation, or deglycosylation of amino acid residues. These IVPS, referred to as controllable intervening protein sequences (CIVPS), are therefore useful in controlling the splicing reaction.

In one preferred embodiment, a DNA sequence encoding a CIVPS is inserted into a DNA sequence encoding a target protein such that both coding sequences form a continuous open reading frame. Thereafter, expression of this fusion DNA is utilized to produce the modified target protein. In another embodiment, the modified protein so produced is subjected to predetermined conditions under which the CIVPS will be excised. In certain embodiments, the CIVPS is inserted into a region of the target protein which renders the target protein substantially inactive and excision of the CIVPS restores the activity of the target protein.

Preferred CIVPSs include CIVPS1 and 2 obtainable from *T. litoralis* (also sometimes referred to as Vent IVPS 1 and 2 or IVS1 and 2) and CIVPS 3 obtainable from *Pyrococcus sp.*(also sometimes referred to as Deep Vent IVPS1). These CIVPSs are capable of excision, i.e., removal via protein splicing, from modified proteins upon an increase in temperature.

In accordance with the present invention, it has also been found that certain CIVPS amino acid residues and at least the first downstream amino acid residue modulate the splicing reaction and that modification of these residues decrease or stop the splicing reaction. These residues have been shown to be conserved in other IVPSs. Modification of such residues can be used to convert a IVPS to a CIVPS.

The potential uses for the modified proteins and CIVPSs of the present invention are manifold. These include, for example, control of a target protein's enzymatic activity, purification of modified proteins using antibodies specific to the CIVPS by affinity chromatography and production of proteins that are toxic to host cells.

BRIEF DESCRIPTION OF THE DRAWINGS

FIG. 1 depicts the amino acid sequence (SEQ ID NO: 30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39). of proposed protein splice junctions. Amino-terminal (top) and carboxy-terminal (bottom) splice junctions are shown with splice sites indicated by arrows and conserved or similar amino acids boxed.

DETAILED DESCRIPTION OF THE INVENTION

Figure 2:
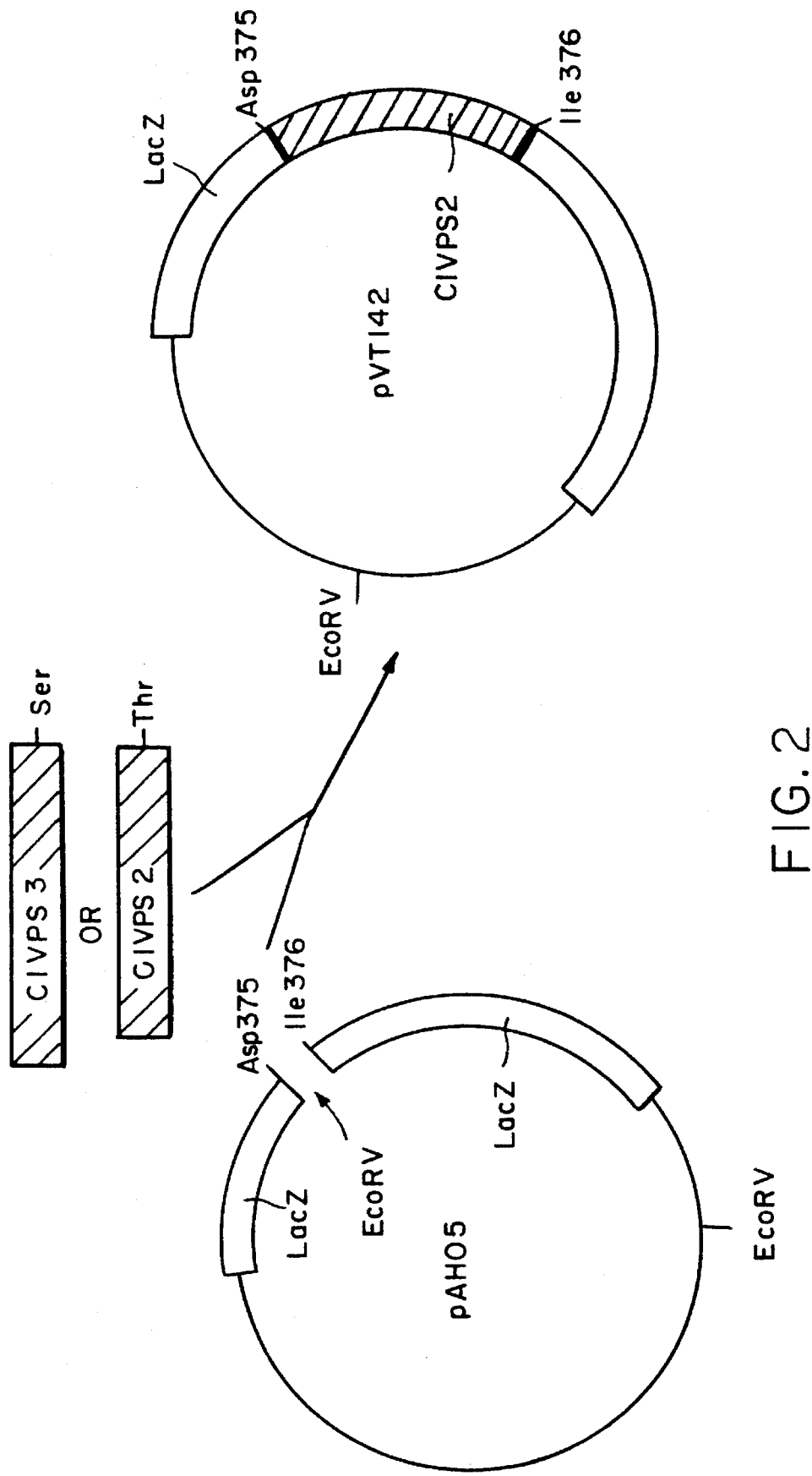
FIG. 2 illustrates insertion of IVPS into the EcoRV site of the beta-galactasidase gene. PCR products of either Deep Vent IVPS1 (CIVPS3) or Vent IVPS2 are ligated to EcoRV digested pAHO5 between the Asp and Ile residues of beta-galactosidase to produce a modified beta-galactosidase product.

The present invention is directed to modified proteins and methods of their production. The modified proteins comprise a controllable intervening protein sequence (CIVPS) inserted into a target protein, the CIVPS being capable of excision from the modified protein under predetermined conditions, i.e., increase in temperature, exposure to light, unblocking of amino acid residues by dephosphorylation or deglycosylation. If desired, the modified protein can be subjected to these conditions. The CIVPS may also be inserted into a region that substantially inactivates target protein activity.

Intervening protein sequences (IVPS) are internal in-frame peptide segment found within a precursor protein which is removed or excised via protein splicing to form the native protein. IVPSs have been described in the *TFPI allele* from *Saccharomyces cerevisiae* [Hirata et al., supra; Kane et al., supra] and rec A gene from *Mycobacterium tuberculosis* [Davis et al., supra; Davis et al., supra (1992)]. The disclosure of these references are herein incorporated by reference.

CIVPSs of the present invention include any intervening protein sequence in which the splicing reaction can be controlled, either by inherent properties of the native IVPS, such as an increase in temperature, or by modifications made to an IVPS that allow the splicing reaction to be controlled.

The Vent DNA polymerase gene from the hyperthermophilic archaea *Thermococcus litoralis* contains two in-frame IVPSs, IVPS1 (CIVPS1) and IVPS2 (CIVPS2), [Perler, et al. supra] that can be deleted at the DNA level without affecting the kinetic and biochemical properties of the expressed polymerase. Correct processing of the Vent DNA polymerase gene containing both IVPSs occurs in the native archaea, *T. litoralis*. In addition, correct processing of expression constructs lacking IVPS1 has been observed in eubacterial *E. coli* [Perler, et al., supra] and in eukaryotic baculovirus-infected insect cell. Furthermore, rabbit reticulocyte and *E. coli* in vitro transcription/translation systems correctly remove IVPS2 sequences to produce the mature polymerase. While not wishing to be bound by theory, it is believed that the Vent and Deep Vent IVPSs are self splicing.

The nucleotide sequence for the Vent DNA polymerase gene is set out in the Sequencing Listing as SEQ ID 7. The nucleotide sequence for CIVPS1 is from nucleotide 1773 to 3386. The nucleotide sequence for CIVPS2 is from nucleotide 3534 to 4703. CIVPS1 and CIVPS2 can be obtained from phage NEB 619, which was deposited with the American Type Culture Collection (ATCC) on Apr. 24, 1990 and received ATCC accession number 40795.

A third IVPS (CIVPS3 or DV IVPS1), has been found by the present inventors in the DNA polymerase gene of the thermophilic archaebacteria, Pyrococcus species (isolate GB-D). The Pyrococcus DNA polymerase is sometimes referred to as Deep Vent DNA polymerase. The nucleotide sequence of the Deep Vent DNA polymerase is set out in the Sequence Listing as SEQ. ID 12. The nucleotide sequence for CIVPS3 is from 1839 to 3449. CIVPS3 can be obtained from plasmid pNEB #720 which was deposited with the ATCC on Oct. 1, 1991 and received ATCC accession number 68723.

In accordance with the present invention, it has been found that the above CIVPS1, CIVPS2 and CIVPS3 are capable of excision from modified proteins upon an increase in temperature. For example, the CIVPSs are excised at reduced rates at temperatures from 37° C. and below, but undergo excision more efficiently at temperatures from about 42° C. to 80° C. Preferred excision temperatures are between about 42° C. and 60° C. Most preferably, predetermined excision conditions are experimentally determined taking into consideration temperatures at which the target protein will not denature or undergo thermal inactivation. The modified proteins can be subjected to the predetermined temperatures for a period of time ranging from less than one minute to several hours. In certain situations, depending on the thermal sensitivity of the target protein, it may be desirable to increase the incubation time period while decreasing the temperature.

Other IVPSs can be isolated, for example, by identifying genes in which the coding capacity is significantly larger than the observed protein and that encodes a protein sequence not present in the mature protein. A protein containing an IVPS can be distinguished from a protein having a "pre-pro" precursor in that the mature protein will still have the N-terminal and C-terminal sequences of the IVPS containing precursor. Additionally, IVPSs can be detected by the absence of motifs that are conserved in certain protein families, e.g., DNA polymerases. The absence of such a motif may indicate that an IVPS is interrupting that motif [Perler et al., supra]. Once identified, the DNA encoding the IVPS can be isolated and manipulated using standard DNA manipulation techniques.

CIVPSs of the present invention also include IVPSs which have been modified such that the splicing reaction can be controlled. As shown in FIG. 1, (SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39) the aligned splice junctions of known protein splicing IVPSs reveal several similarities. In particular, —OH and —SH side chains are found on residues at the N-terminal side of both splice junctions, preceded by the dipeptide His-Asn at the downstream splice junction. In accordance with the present invention, it has been found that single amino acid changes at the serine 1082 of CIVPS2 slowed or blocked the protein splicing reaction. Specifically, the threonine substitution mutant displayed 10% of the polymerase activity of the wild-type enzyme, while the cysteine and alanine substitution mutants gave no detectable activity. While not wishing to be bound by theory, it is believed that hydroxyl/sulfydryl groups participate in the splicing reaction and thus modification of these residues modulate the splicing reaction.

Such modification can be accomplished in a number of ways. For example, the sequence surrounding the amino acid residue to be modified may be altered to create a biological phosphorylation site allowing it to be a substrate for specific kinases and phosphatases. Examples of protein kinase include, for example, casein kinase II, cAMP-dependent protein kinase, cdc2, and pp60$^{c-src}$ [Pearson and Kemp, Methods in Enzymology 200:62 (1991)]. Examples of phosphatases include, for example, protein phosphatase 2A, lambda phosphatase, and the yop phosphatase from Yersinia [Tonks, *Current Opinion in Cell Biology*, 2:1114 (1990)].

Using CIVPS2 as an example, as set forth in Example 6C, an arginine residue was placed at position 1079 to create a consensus Calmodulin-dependent protein kinase II site [XRXXS*; Pearson et al., supra.] The protein splicing reaction may then be regulated by the degree of phosphorylation, using a kinase to create phosphoserine and block the splicing, and phosphatases to remove the phosphate, restoring the wild type serine and, consequently, protein splicing.

Additionally, critical splice junction residues, i.e., serine 1082, can be modified chemically such that the splicing reaction is blocked. This can be accomplished using, for example, a variation of the unnatural amino acid mutagenesis methodology developed by Schultz [Noren et al., Science 244:182 (1989); Ellman et al., Methods in Enzymol. 202:301 (1991)]. Using this method one of the amino acid residues involved in the splicing reaction is replaced by a synthetic derivative in which the chemical functionality of the side-chain is "masked" by a chemically or photolytically removable group. Briefly, using CIVPS2 as an example, as set forth in Example 6D, an amber stop codon (TAG) was introduced into a gene containing IVPS2 at the position corresponding to a residue involved in splicing. This gene can then added to an in vitro transcription-translation system, for example, an *E. coli* system, along with an amber suppressor tRNA that has been chemically aminoacylated with the desired blocked amino acid derivative. During translation, the blocked amino acid is site-specifically incorporated into the growing peptide at the position corresponding to the amber codon.

Using CIVPS2 as an example, this strategy can be applied to S1082 and T1472, which are found at the upstream and downstream splice junction of CIVPS2, respectively. Both contain hydroxyl side chains that are postulated to act as nucleophiles during the splicing reaction, on the basis of similar nucleophilic residues, including Cys, found at the splice junction at other examples of protein splicing. See, FIG. 1. (SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39). These residues can be replaced with a photoactivatable derivative of serine in which the side chain oxygen is blocked with the o-nitroveratryloxycarbony(NVOC) group, which can be removed by brief irradiation with 350 nm light. The precursor protein thus synthesized would be unable to splice until the protein was irradiated with 350 nm light, at which point the hydroxyl functionality would be exposed and the splicing reaction could proceed normally. [Mendel et al., *J. Am. Chem. Soc.* 113:2758 (1991)].

It has been shown that IVPS1 and IVPS2 each encodes an endonuclease, I-Tli-II and I-Tli-I, respectively. In addition, DV IVPS1 also encodes an endonuclease, I-PspI, which is inserted at the same position in the DV DNA polymerase gene as IVPS1 and is 62% identical to the IVPS1 gene. It has been found that the IVPS open reading frames in Tfp1, *M. tuberculosis* rec A, Vent and Deep Vent DNA polymerase have protein sequence similarity to homing endonucleases, a class of intron-encoded proteins capable of cleaving alleles which lack the intron. [Hirata et al., supra, Kane et al., supra, Davis et al., supra, Perler et al., supra.]

Certain host cells may not be able to tolerate the gene product of the CIVPS and thus, in some embodiments it may be preferable to inactivate the endonuclease function. In accordance with the present invention it has been shown that protein splicing can occur when the CIVPS endonuclease function has been inactivated. Such inactivation can be accomplished in a variety of ways, including for example, random mutagenesis, deletion or insertional inactivation, or site directed mutagenesis. Preferably, the endonuclease function is inactivated by site directed mutagenesis. I-Tli-I share sequence similarity with other "homing endonucleases" in the pair of characteristic dodecapeptide motifs [Cummings et al., *Curr. Gent.*, 16, 381 (1989)]. As shown in Example 6B, endonuclease activity was inactivated by oligonucleotide-directed mutagenesis of a single residue (aspartate 1236 to alanine) within one of these motifs. Substitution of alternative residues could also reduce or abolish endonuclease activity without affecting protein splicing. Inactivation of endonuclease function has been shown to increase the stability of constructs carrying the modified proteins.

Target proteins which can be used in accordance with the present invention include, for example, enzymes, toxins, cytokines, glycoproteins and growth factors. Many such proteins are well known to the skilled artisan. The amino acid and nucleotide sequence of such proteins are easily available through many computer data bases, for example, GenBank, EMBL and Swiss-Prot. Alternatively, the nucleotide or amino acid sequence of a target protein can be determined using routine procedures in the art.

If it is desirable to substantially inactivate target protein activity, the CIVPS is inserted into a region(s) that will inactivate such activity. Such regions are well know to the skilled artisan and include, for example, binding sites, enzyme active sites, the conserved motifs of proteins, e.g., DNA polymerases, and dimerization or multimerization sites. Alternatively, the CIVPS may be inserted randomly and the activity of each modified protein measured until the desired level of activity is obtained. Preferably, such a modified protein has about a 50% reduced level of activity compared to the native protein. More preferably about 75%. Still more preferably greater than 99%.

The CIVPS may be inserted into the target gene by any number of means. Preferably, to assure proper protein splicing if the CIVPS is excised, it is important to insert the CIVPS immediately before a proper splice junction residue because excision of the CIVPS leaves that amino acid at the splice junction. This can be accomplished by either inserting the CIVPS immediately before the appropriate splice junction amino acid or by modifying the CIVPS such that it "brings" the appropriate amino acid with it.

For example, CIVPS1, 2 or 3 can be inserted immediately before the appropriate splice junction amino acids, for example, serine, threonine or cysteine residues, most preferably before serine or threonine. See, FIG. 1. Such sites are readily available in most target proteins.

In certain situations, such as when the target protein is a toxin, it may be desirable to further control protein splicing by adding a secondary control. This may be accomplished by inserting the CIVPS before a less optimal amino acid, for example, one that the CIVPS does not normally precede and thus may slow down the splicing reaction.

As set forth above, insertion can be at any site within the target protein if the CIVPS "brings" the appropriate downstream amino acid with it. This can be accomplished by creation of CIVPS DNA having a codon for the desired downstream amino acid. Methods for producing such DNA are set out in detail below. This DNA can then be inserted at any site within the target DNA. Upon protein splicing of the resulting modified protein, the extra residue brought by the CIVPS will be left behind. Thus, if activity of the final product is important, the skilled artisan must takes steps to assure that the extra residue will not be left in an area of the target protein that will adversely affect activity.

The CIVPS may be inserted into the target protein by chemically synthesizing the primary amino acid sequence of the target protein, including the CIVPS, inserted at any desired site, using standard methods [e.g., see Hunkapiller, et al., Nature 310:105 (1984)] and a commercially available protein synthesizer.

Alternatively, a DNA sequence encoding a CIVPS is inserted in a DNA sequence encoding for a target protein such that both coding sequences form a continuous reading frame. This can be accomplished using a variety of methods known to the skilled artisan, several of which are set out below.

For example, the CIVPS DNA is inserted into any restriction enzyme site that makes a blunt cut in the target gene and which is in frame. This can be accompanied by first, synthesizing an CIVPS DNA fragment with a threonine codon (for Vent IVPS2) or a serine codon (for Deep Vent IVPS1 or Vent IVPS 1) at its 3' end. This fragment is then ligated in-frame to a linear plasmid cut to blunt ends by the restriction endonuclease. Using the lacZ DNA sequence, for example, an EcoRV site can be used to insert Vent IVPS2 or Deep Vent IVPS1 between residue 375 (aspartic acid) and 376 (isoleucine). See, FIG. 2. However, as discussed above, using this method, if the CIVPS is excised an extra residue is expected to remain at the splice junction and therefore depending on where the CIVPS is inserted, the resulting protein may not have the same function or structure as the native protein.

The CIVPS DNA could also be inserted by making silent mutations (preserving the amino acid residue) near one end or both ends of the CIVPS to create restriction sites compatible with the target gene. Using CIVPS2 as an example, a BspEI restriction site can be made near the 5' end and a SpeI restriction site near its 3' end, by silent mutations. Using PCR primers overlapping the new restriction sites and continuing through the beginning of the lacZ target gene at either asp 594 or thr 595, one can generate a lacZ fragment with compatible BspE1 and SpeI restriction sites. Then, the CIVPS is inserted between an aspartic acid codon (residue 594) and a threonine codon (residue 595) within the lacZ coding region. DNA fragment(s) can be synthesized from both the CIVPS and the target gene by PCR with their ends at the insertion site overlapping with the termini of the CIVPS, therefore, including the same restriction sites. After appropriate restriction endonuclease treatment, DNA fragments with compatible ends can then be ligated to create a fusion gene. Since no extra residue would be left after excision of the CIVPS, native polypeptide will form when splicing occurs. Preferably, the restriction site being created is unique within the CIVPS and within the target gene to avoid ligation of multiple fragments and thus, complicated screening procedures.

If the plasmid vector carrying the target gene sequence is relatively small, for example, less than about 5 Kb, a linear form of the plasmid can be generated using PCR, and then the linear plasmid can be ligated to the CIVPS gene. Using this method the CIVPS gene can be inserted at any location in the target gene as follows: First, plasmid DNA containing the target gene can be synthesized by PCR using a pair of primers starting at the insertion site, for example, serine or threonine codons for CIVPS1, 2 and 3, or any codon if the CIVPS also brings the appropriate downstream amino acid. Next, the CIVPS gene (with or without serine or threonine) can be ligated to the linear plasmid DNA (without the serine or threonine codon). The required splice junction amino acids (serine or threonine) can be positioned on either the CIVPS fragment or on the target gene. The advantage of having the required amino acid on the CIVPS fragment when placing upstream of an endogenous serine or threonine is that the self-ligated vector DNA (without the CIVPS insert) may only express a deficient product of the target gene because of the deletion of the serine or threonine in the coding region. This may aid in phenotype selection for the fusion construct if the fusion protein can splice to produce a functional product.

The fusion DNA encoding the modified protein can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. For instance, when expressing a modified eukaryotic protein, it may be advantageous to use appropriate eukaryotic vectors and host cells. Expression of the fusion DNA results in the production of the modified proteins of the present invention.

Once obtained, the modified proteins can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis.

If desired, the modified proteins can be subjected to predetermined conditions under which the CIVPS is excised. Such conditions depend on the CIVPS used. For example, CIVPS 1, 2 and 3 are capable of excision by subjecting the modified protein to increased temperature, 42° C.–80° C. most preferably, 42° C.–60° C. This can be accomplished using any know means, for example a water bath or a heat generating laser. The time period for incubation can range from less than one minute to greater than several hours. As discussed above, in certain situations, depending on the thermal sensitivity of the target protein, it may be desirable to increase the incubation period while decreasing the temperature. In addition, if in vivo splicing is desired, lower temperatures are preferred.

The present invention may be used to produce proteins that are highly toxic to the host cells by using the CIVPS to modifying a toxic target protein such that the modified protein is non-toxic. This can be accomplished, for example, by inserting the CIVPS into a region(s) responsible for toxicity. After isolation, the non-toxic modified protein can then be subject to predetermined condition under which the CIVPS will excise and the resulting toxin can be isolated.

If a protein is extremely toxic to a host cell it may be desirable to produce that protein using a method referred to as "transplicing". Using this method the toxic protein is produced in two or more pieces in separate host cells. Each piece being modified by insertion of a CIVPS. For example, a first modified protein can be produced comprising an amino portion of a target protein to which is inserted at its carboxy terminus an amino terminal fragment of a CIVPS, thereafter a second modified protein comprising the remaining portion of the target protein into which is inserted at its amino terminus the remaining fragment of CIVPSs. Alternatively, overlapping CIVPS fragments can be used. Each modified protein is then isolated from the host cells and incubated together under appropriate conditions for splicing of the CIVPS. This results in a ligated target protein. By dividing the target protein in two different hosts, there is no possibility that even a minute fraction will splice in vivo, adversely affecting the host. In addition, the entire CIVPS may be inserted on either side of the splice junction of the first modified protein and the remaining target protein fragment added to the splicing mixture.

The CIVPSs of the present invention can also be used to isolate modified proteins by use of affinity chromatography with antibodies specific to the CIVPS. For example, monoclonal or polyclonal antibodies can be generated having binding affinity to a CIVPS using standard techniques. These antibodies can then be utilized in affinity chromontography purification procedures to isolate a modified protein. After purification, if desired, the modified proteins can be subjected to predetermined conditions under which the CIVPS will undergo excision.

The present invention is further illustrated by the following examples. These examples are provided to aid in the understanding of the invention and are not construed as a limitation thereof.

Example 1

Synthesis of IVPS cassettes for insertion into blunt sites between target gene codons.

DNA fragments or cassettes for in-frame insertion of IVPSs into the lacZ coding region or any other target gene can be prepared by polymerase chain reaction (PCR) with or without the first downstream external protein sequence (EPS) codon. The native downstream residues are serine for Deep Vent IVPS1 and Vent IVPS1 or threonine for Vent IVPS2. It has been found that IVPS2 can splice if it precedes a threonine or cysteine, although at reduced levels. Although not wishing to be bound by theory, it is believed that all the IVPSs can splice to some extent when preceding either serine, threonine or cysteine. Cassettes including the downstream serine or threonine can be inserted at any desired location in the target gene including preceding a serine or threonine. In the latter constructions, one may delete the serine or threonine from the target gene and substitute it with the incoming residue on the cassette. Cassettes lacking downstream serines, threonines or cysteines may be inserted prior to a serine, threonine or cysteine in the target gene.

The following protocol describes the production of cassettes for Deep Vent IVPS1 (CIVP3) and Vent IVPS2 (CIVPS2) (endo$^+$ and endo$^-$ versions), including the first downstream EPS codon.

The PCR mixture contains Vent DNA polymerase buffer (NEB), supplemented with 2 mM Magnesium sulfate, 400 uM of each dNTP, 0.9 uM of each primer and 40 ng plasmid DNA and 2 units of Vent DNA polymerase in 100 ul. Amplification was carried out by using a Perkin-Elmer/Cetus thermal cycler at 94° C. for 30 sec, 48° C. for 30 sec and 72° C. for 2 min for 30 cycles. Deep Vent IVPS1 was synthesized from pNEB #720 (ATCC No. 68723) which has a 4.8 Kb BamHI fragment containing the Pyrococcus sp. DNA polymerase gene inserted into the BamHI site of pUC19. Vent IVPS2 was synthesized from pV153-2 which has a 1.9 kb EcoR1 fragment (2851–4766) of the Vent DNA polymerase gene sequence in the vector Bluescribe SK—(Stratagene). Alternatively, pNEB671 (ATCC No. 68447) can also be used for IVPS2. pAMQ29 is an endonuclease-deficient derivative of pV153-2, carrying an amino acid substitution (aspartic acid 1236 to alanine) within the Vent IVPS2 coding region. Primers 5'-AGTGTCTCCG-GAGAAAGTGAGAT-3' (SEQ ID NO:3) (Vent IVPS2 forward, 3534–3556, a substitution of A3542 to C) and 5'-AG-TATTGTGTACCAGGATGTTG-3' (SEQ ID NO:4) (Vent IVPS2/Thr reverse, 4685–4706) were used to synthesize endo$^+$or endo$^-$ Vent IVPS2 fragment (1173 bp) with a threonine codon at its 3' terminus. Primers 5'-AGCATTT-TACCGGAAGAATGGGTT-3' (SEQ ID NO:5) (DV IVPS1 forward, 1839–1862) and 5'-GCTATTATGTGCATAGAG-GAATCCA-3' (SEQ ID NO:6) (DV IVPS1/Ser reverse, 3428–3452) were used to synthesize the Pyrococcus sp. (or Deep Vent) IVPS1 fragment (1614 bp) with a serine codon at its 3' end. Reverse primers lacking the final three nucleotides could be used to generate IVPS fragments lacking the C-terminal serine or threonine.

The PCR samples were extracted with phenol and chloroform, precipitated in 0.3M NaAc and 70% ethanol at −20° C. for overnight, recovered by spinning at 10K for 10 min in a microfuge, dried and each resuspended in 30 ul of distilled water, loaded on a 1% agarose gel for electrophoresis at 60 volts for 15 hours. The gel slices that contain the PCR-amplified fragments were placed in a 1% low melting agarose gel for electrophoresis at 80 volts for 2 hours. DNA fragments were recovered from the low melting agarose gel by incubation in 0.5 ml of TE buffer (10 mM Tris-HCl/0.1 mM EDTA, pH8.0) at 65° C. for 30 min, extractions with phenol, phenol-chloroform (1:1 mixture) and chloroform, precipitation in 0.6M NaAc (pH5.2) and 50% isopropanol at −20° C. for overnight. DNA was spun down, washed with 70% ethanol, dried and resuspended in 15.5 ul distilled water.

Phosphorylation of the IVPS DNA fragments was performed at 37° C. for 60 min with 2 ul of 10× polynucleotide kinase buffer (NEB), 15.5 ul of purified DNA, 2 ul 10 mM ATP, and 5 units of T4 Polynucleotide kinase (NEB) in 20 ul. The samples were heated in a 65° C. water bath for 10 min. After addition of 80 ul of TE buffer (10 mM Tris-HCl/0.1 mM EDTA, pH8.0), the samples were sequentially extracted with phenol, phenol-chloroform (1:1 mixture) and chloroform. DNA was precipitated in 2.5M $NH_4Ac$ and 70% ethanol at −70° C. for 3.5 hours, pelleted by spinning at 10K for 10 min in a microfuge, washed with cold 70% ethanol, dried and resuspended in distilled water (20 ul for Vent IVPS2 or Deep Vent IVPS1 DNA, 10 ul for Vent IVPS endo$^-$ DNA).

EXAMPLE 2

In-frame insertion of IVPS in a restriction enzyme linearized plasmid, such as one encoding beta-galactosidase.

In this example, we describe how the IVPS cassettes can be cloned into a target gene by inserting the cassette at a restriction enzyme site which makes a blunt cut in the target gene between 2 codons. The cassette can carry a C-terminal serine, cysteine or threonine if necessary. This protocol works best if the restriction enzyme cuts the target gene vector once or twice. As an example, we describe insertion into the EcoRV site of the lacZ gene (FIG. 2).

Preparation of EcoRV-linearized pAHO5.

pAHO5 carries the entire lacZ gene sequence on a 3.1 kb BamHI-DraI fragment from pRS415 (Simons, et al., *Gene*

(1987) 53:85–96) inserted between BamHI and SmaI sites in the polylinker of pAGR3 downstream of a tac promoter. The tac promoter is a transcription control element which can be repressed by the product of the lacI$^q$ gene and be induced by isopropyl beta-D-thiogalactoside (IPTG). The 5.9 Kb vector pAHO5 (NEB) also has a transcription terminator sequence upstream of the tac promoter and the polylinker, and the E. coli lacI$^q$ gene. pAHO5 contains two EcoRV recognition sequences. EcoRV leaves blunt ends at its cleavage site. One of the EcoRV cleavage sites cuts within the lacZ coding region between the 375th codon (aspartic acid) and the 376th codon (isoleucine) and is planned as the site for in-frame insertion of the IVPS fragments. The other site is located 3.2 Kb downstream within the E. coli lacI$^q$ gene. The plasmid is cut partially to produce some molecules in which only one of the EcoRV sites has been cleaved. These linear plasmids are purified. The IVPS cassettes will be randomly cloned into either EcoRV site. Therefore, the resultant recombinants must be screened for orientation and insertion into the proper EcoRV site. DNA was partially digested by incubation of 15 ug of pAHO5 DNA with 40 units of EcoRV (NEB) in 100 ul of 1×NEB buffer 2 at 37° C. for 60 min. 20 ul agarose gel loading dye was added to the sample after the sample was heated to 65° C. for 10 min to inactivate EcoRV. DNA fragments were separated by electrophoresis on a 1% low melting agarose gel. Linearized pAHO5 plasmid DNA was recovered from the low melting agarose gel as described in example 1 and resuspended in 44.6 ul of distilled water.

Dephosphorylation of EcoRV-linearized pAHO5 was carried out in 50 ul of 1×NEB buffer 2 at 50° C. for 60 min. in the presence of 2 ug DNA and 4 units of Calf Intestinal Alkaline Phosphotase (NEB). The sample was heated in a 65° C. water bath for 30 min after addition of 0.5 ul of 0.5M EDTA (pH8.0) and extracted with phenol, phenol-chloroform (1:1 mixture), and chloroform. DNA was precipitated in 0.75M NH4Ac and 70% ethanol for 2 hours, recovered as described in example 1, and resuspended in 20 ul of distilled water.

Construction of IVPS-lacZ fusion genes.

Ligation of dephosphrylated pAHO5 DNA with phosphorylated IVPS fragments was carried out at 16° C. for 15 hours in 20 ul volume with addition of 8.6 ul distilled water, 2 ul of 10X T4 DNA ligase buffer (NEB), 4 ul of 0.1 ug/ul dephosphorylated pAHO5 DNA, 5 ul IVPS DNA prepared as described above (0.25 ug of Vent IVPS2, 0.4 ug Deep Vent IVPS1 or 0.25 ug of Vent IVPS2 endo$^-$) and 160 units of T4 DNA ligase (NEB).

E. coli strain RR1 was transformed by mixing 100 ul of competent RR1 cells with 10 ul of ligation sample on ice for 30 min., heating at 42° C. for 2 min., chilling on ice for 5 min., adding 0.8 ml LB media (10 grams/liter tryptone, 5 grams/liter yeast extract, 10 grams/liter NaCl, 1 gram/liter Dextrose, 1 gram/liter MgCl$_2$. 6H$_2$O, pH7.2 at 25° C.) and incubating at 30° C. for 45 min. The samples were plated onto LB plates, supplemented with 100 ug/ml ampicillin at 0.2 ml per plate. After incubation overnight at 30° C., about 150–300 colonies per plate were observed.

Colony hybridization was utilized to screen for clones that carry recombinant plasmids. The Vent IVPS2 forward primer and the Deep vent IVPS1 forward primer, described in example 1, were radio-labeled with T4 polynucleotide kinase and used as hybridization probes. Colonies were lifted onto nitrocellulose and treated for 5 min. in each of the following solutions: 10% SDS, 0.5M NaOH/1.5M NaCl, 0.5M Tris-HCl (pH7.5)/0.5M NaCl (twice) and 2XSSC (twice). The nitrocellulose filters were dried at room temperature for 1 hour, baked in vacuum at 80° C. for 2 hours, soaked in 6×SSC for 5 min and washed in a solution of 50 mM Tris-Cl (pH8.0), 1M NaCl, 1 mM EDTA and 0.1% SDS at 42° C. for 2 hours. After treatment at 42° C. for 4 hours in 6×NET, 5×Denhardt's, 0.5% SDS and 25 ug/ml of denatured salmon sperm DNA, the filters were incubated with the radiolabeled oligomer probe under the same conditions for 16 hours and then washed in 6×SSC at room temperature three times for 15 min, twice at 42° C. for 2 min and twice at 50° C. for two min, followed by autoradiogram. 36 clones were found to hybridize to the corresponding oligomer probes.

The positive clones were further analyzed to determine insert location by PCR amplification of plasmid DNA extracted from these clones, using the Vent IVPS2 forward primer (or the Deep Vent IVPS1 forward primer) described in Example 1, and a lacZ reverse primer (5'AGGGTCGA-CAGAGATTTGATCCAGCG-3') (SEQ ID NO:7) complementary to the lacZ coding sequence (1417–1440, with a G:T mismatch at 1437) 392 nt downstream of the insertion site. PCR reactions from 14 clones produced the corresponding DNA fragments. Clones pVT133, 138, 139, 141, 142, and 144 contain the 1.1 Kb Vent IVPS2 insert, and pVTE 834, 836, 839 and 841 contain the Vent IVPS2 (endo$^-$) insert, all yielding DNA fragments of approximately 1.1 kb. Clones pDVS 712, 742, 745 and 746 carry the 1.6 Kb Deep Vent IVPS1 insert, producing DNA fragments of about 2.0 Kb.

Expression of the IVPS-lacZ fusion genes.

The clones were further examined by their ability to express fusion (modified) proteins with inducer IPTG.

The clones were cultured in LB medium supplemented with 100 ug/ml ampicillin at 30° C. until OD$_{600nm}$ reached 0.5. To prepare lysate from uninduced cells, 1.5 ml of culture was pelleted and resuspended in 100 ul of urea lysis buffer, followed by boiling for 10 min. After addition of IPTG to a final concentration of 0.3 mM, the cultures were grown at 30° C. for 4 additional hours. Cells from 1.5 ml culture were pelleted and then lysed with 250 ul of the urea lysis buffer after induction for 2 hours and 4 hours. Protein products were analyzed by Coomassie Blue stained gels. Three of the Vent IVPS2-lacZ fusion constructs (pVT139, 142 and 144) and all four Vent IVPS2 (endo$^-$)-lacZ fusion constructs showed a major product of about 162–165 KDa, the expected size for a Vent IVPS2-beta-galactosidase fusion protein. All four Deep Vent IVPS1-lacZ fusion clones expressed a larger product of 173–178 KDa, the expected size for the Deep Vent IVPS1-beta-galactosidase fusion protein.

The identity of the Vent IVPS2 fusion proteins from pVT142 and 144, and pVTE836 and 839 was further analyzed by western blots using antibody raised against I-Tli-I (NEB) or beta-galactosidase (Promega). Samples were electrophoresed on 4–20% SDS gels (ISS, Daichi, Tokyo, Japan) with prestained markers (BRL), transferred to nitrocellulose, probed with antisera (from mouse), and detected using alkaline phosphate-linked anti-mouse secondary antibody as described by the manufacturer (Promega). A band of approximately 160 KDa from all four clones being examined reacts with both sera and migrates at the same location as the Coomassie Blue stained band. Deep Vent IVPS1 fusions were also examined. Western blot analysis of pDVS712 and 742 using sera against beta-galactosidase and I-PspI (the protein product of Deep Vent IVPS1) yielded the predicted major band at about 168–175 KDa, identical to the Coomassie Blue stained band.

EXAMPLE 3

Thermal control of protein splicing in Beta-galactosidase-IVPS fusions.

The constructs described above (IVPSs inserted into the lacZ EcoRV site) yield fusion (modified) proteins after induction. The IVPS protein can be excised from the fusion protein to generate a ligated target protein (active beta-galactosidase) and free IVPS endonuclease by incubation at elevated temperatures.

Splicing is controllable by temperature induction: Beta-galactosidase activity in crude extracts increases in response to temperature shift.

Crude extracts were prepared from cultures of RR1 (the *E. coli* host) and RR1 containing pAHO5 (the non-fusion beta-galactosidase parent plasmid described in Example 2) or the fusion constructs, pVT142 (Vent IVPS2 or CIVPS2), pVTE836 (Vent IVPS1 endo⁻) or pDVS712 (Deep Vent IVPS1 or CIVPS 3) by the following steps. A single colony was inoculated in 10 ml LB medium supplemented with 100 ug/ml ampicillin, incubated at 30° C. overnight, subcultured in 1 liter LB medium (100 ug/ml ampicillin) at 30° C. to $OD_{600nm}$ about 0.5 and induced with IPTG at 0.3 mM at 30° C. for 2 hours. Cells were spun down and resuspended in 100 ml of LB, sonicated for 3 min at 4° C. and spun at 7000 rpm for 15 min. The supernatants were recovered and stored at −20° C. 7.5 ml aliquots of crude extracts were incubated in 42° C. or 50° C. water baths; 1 ml aliquots were taken at 1, 2 and 12 hours for pVT142 and pVTE836 extracts or 0.5, 1, 2, 4 and 16 hours for pDVS712, pAHO5 or RR1 extract.

Figure 3A:
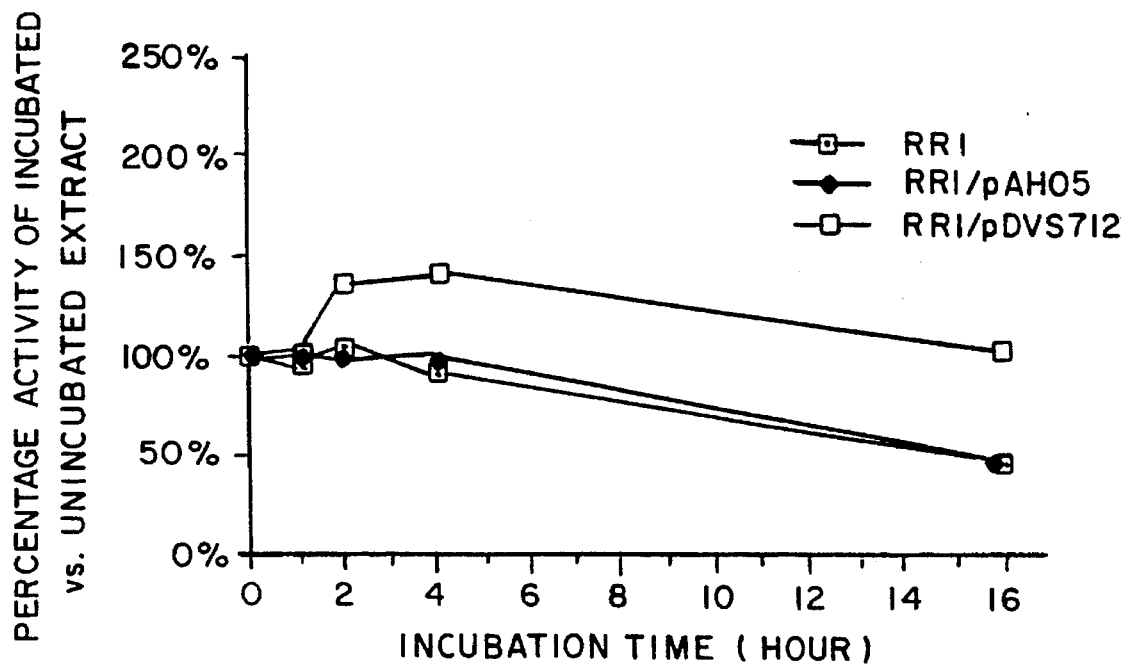
FIG. 3 are graphs showing that splicing of modified beta-galactosidase yields active beta-galactosidase. Incubation of crude extracts from hosts expressing the indicated IVPS-beta-galactosidase fusion proteins at 42° C. yields an increase in enzyme activity with time. Whereas incubation at 42° C. with the host alone (RR1) or an unmodified beta-galactosidase construct (pAHO5) shows no increase in enzyme activity.
Figure 3B:
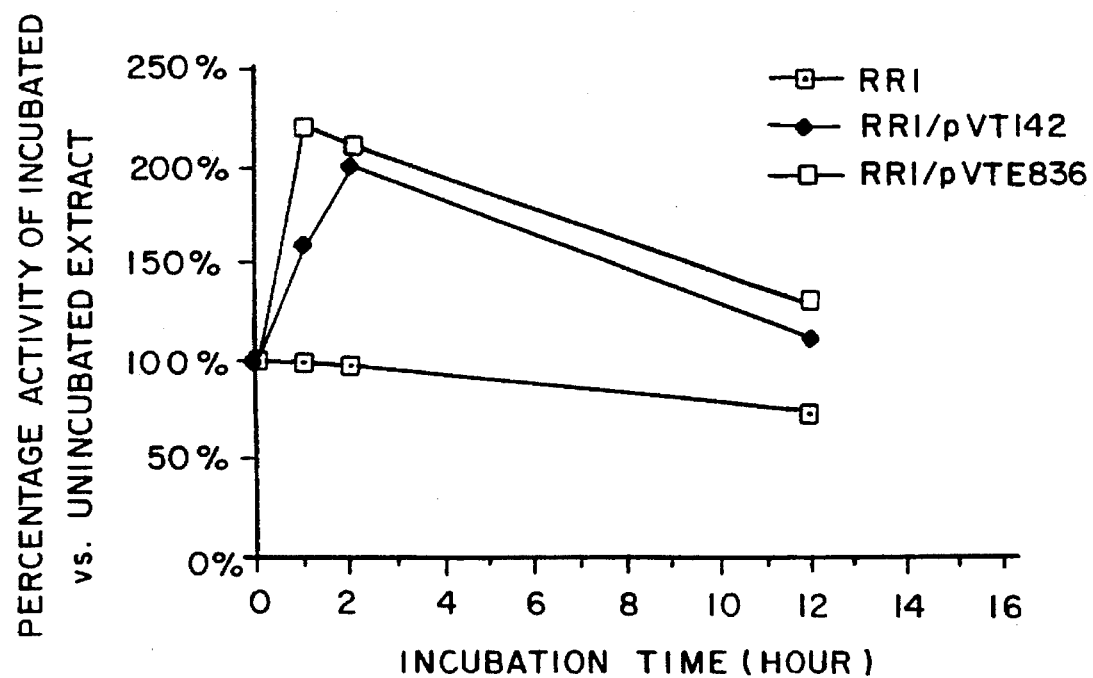

Beta-galactosidase activity was measured according to Miller et al. (Experiments in Molecular Genetics (1972), Cold Spring Harbor, N.Y., Cold Spring Harbor Laboratory). Assay buffer was prepared by mixing Z buffer with 2.7 ul/ml of 2-mercaptoethanol. Substrate o-nitrophenyl-beta-D-galactopyranoside (ONPG) was dissolved in the assay buffer at 4 mg/ml. 0.1 ml of treated or untreated extract was transferred into a test tube containing 0.9 ml of assay buffer and 1 drop of 0.1%SDS and incubated for 5 min at 28° C. 0.1 ml LB medium was used for blank. 0.2 ml of 4 mg/ml ONPG was added to start an assay reaction. When adequate yellow color developed, the reaction was stopped by addition of 0.5 ml of 1M $Na_2CO_3$. The incubation time was recorded and activity was measured on a spectrophotometer at $OD_{420nm}$ and $OD_{550nm}$. The enzymatic activity from the heat-treated extract was calculated as follows. The activity after incubation was divided by the activity of the zero time point; the ratio was then multiplied by 100 to yield a percentage. Comparison of enzymatic activity indicated that while heat treatment had no effect on activity from RR1 or RR1/pAHO5 extract in the first two hours of incubation, all three IVPS-LacZ fusion constructs, pVT142, pVTE836 and, pDVS712, exhibited an increase in enzymatic activity in response to the temperature shift to 42° C. from 143% to 221% of untreated samples (FIG. 3). This increase in beta-galactosidase activity was due to excision of the IVPS and ligation of the two halves of beta-galactosidase, forming more enzyme which was active. The splicing was confirmed by Western blot analysis. Beta-galactosidase activity in RR1 cells comes from expression of the chromosomal gene. The overnight incubation resulted in lower enzymatic activity from all samples, probably due to thermal inactivation of beta-galactosidase (FIG. 3).

Splicing is controllable by temperature induction: Analysis of proteins by Coomassie Blue staining and Western blots.

Analysis of IVPS-lacZ fusion protein synthesis in RR1 cells is complicated by chromosomal expression of beta-galactosidase. Therefore, for ease of analysis, all the constructs were transferred to an *E.coli* host which did not synthesize beta-galactosidase.

Preparation of crude cell extracts from the IVPS-lacZ fusion clones and western blot analysis of heat-treated samples were performed as followings.

The fusion constructs and the lacZ expression vector pAOH5 were introduced into a lacZ-deletion *E. coli* strain ER2267 (NEB) by the standard transformation procedure as previously described. The cultures of ER2267 (50 ml), ER2267/pAOH5 (50 ml), pVT142 or pDVS712 plasmid (each in 1 liter) were grown at 30° C. in LB media, supplemented with ampicillin at 100 ug/ml for plasmid-containing cells. When $OD_{600nm}$ reached between 0.48 and 0.55, inducer IPTG was added into the cultures to 0.3 mM final concentration and the cultures were incubated at 23° C. for 3 additional hours. Cells were spun down, resuspended in 50 ml (for ER2267 or pAHO5-bearing ER2267) or 100 ml (for pVT142- or pDVS712-bearing ER2267) LB media, sonicated for 3 min at 4° C. and spun at 7000 rpm for 10 min. The supernatants were stored at −20° C. Three 5 ml aliquots of each extract were incubated and sampled at 23° C., 42° C. or 50° C. for 16 hours. Aliquots of 0.9 ml were transferred into 1.5 ml microfuge tubes after incubation for 1, 2, 3, 4, 6 hours. 5 ul of untreated or treated extract was mixed with 10 ul of water and 5 ul of 5×sample buffer (0.31M Tris-Cl, pH6.8/10%SDS/25% 2-mercaptoethanol/50% glycerol/0.005% Bromophenol blue) and boiled for 10 min.

Figure 4:
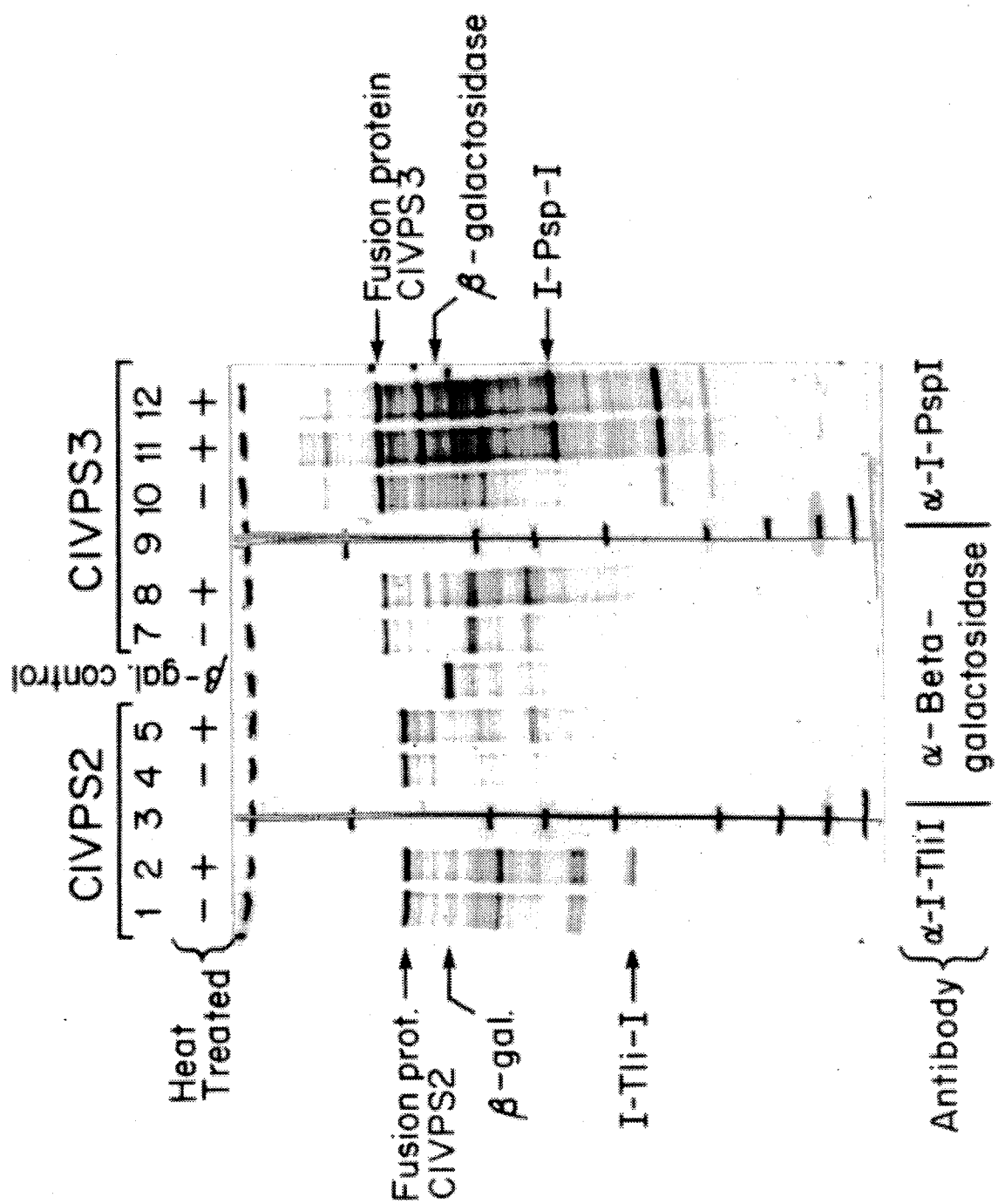
FIG. 4 is a western blot showing the results of temperature controlled protein splicing experiments. CIVPS2 and CIVPS3 were cloned into the EcoRV site of beta-galactosidase. Western blot examination of cell extracts with sera directed against beta-galactosidase or the CIVPS protein (I-TliI and I-PspI, respectively) detects modified beta-galactosidase fusion protein (Lanes 1,4,7,10). Treatment of extracts at 42° C. (Lanes 2,5,8,11) or 50° C. (Lane 12) for 6 hours results in splicing and the production of free CIVPS proteins and unmodified beta-galactosidase (except for retained serine or threonine residue, see text example 2 & 3). Unmodified beta-galactosidase from pAHO5 is in lane 6. Lanes 3 & 9 contain size markers.

5 ul of each sample was loaded on a 4/20% SDS polyacrylamide and electrophoresed at 100 volts for 3–4 hours. Western blots, using antibody raised against beta-galactosidase (Promega) and antibody raised against endonuclease I-Tli-I or I-PspI (NEB), were carried out according to the procedure of Promega. The results showed barely trace amounts of endonuclease present in cells after IPTG induction at 23° C. from both pVT142 and pDVS712 constructs, indicating inefficient excision activity, if any. However, after shifting the ER2267/pVT142 extract to higher temperatures, 42° C. or 50° C., abundant IVPS2 product (I-Tli-I about 42 KDa), identical to the excised endonuclease from the Vent DNA polymerase precursor, was accumulated (FIG. 4). A similar pattern was observed for pDVS712/ER2267 extract treated at 42° C. or 50° C. (FIG. 4), resulting in accumulation of a product of about 60 KDa, expected for the Deep Vent IVPS1 product, I-PspI.

Western blot analysis using antibody against beta-galactosidase indicated that excision of the IVPS domains was coupled with ligation or rejoining of the N-domain and the C-domain of the interrupted beta-galactosidase. The heat-treated samples of both fusion constructs contained a product of 114 KDa, identical in size to full-length beta-galactosidase (FIG. 4). However, this product was only accumulated in small amount in the samples of pVT142, indicating that splicing from this fusion protein is inefficient under these conditions.

The fusion proteins were further tested for their ability to splice at higher temperatures, up to 80° C. The initial reaction rates at different temperatures were compared. The extracts were incubated in 300 ul aliquots in 1.5 ml-microfuge tubes at 42° C., 50° C., 65° C. or 80° C. 20 ul were taken from each heated extract sample at 15 and 30 min and 1, 2, and 4 hours, and mixed with 40 ul of water and 20 ul of 5× sample buffer and boiled for 10 min. Western blot analysis showed that Deep Vent IVPS-beta-galactosidase fusion protein was able to splice at 65° C. and at 80° C., although splicing seems more efficient at 65° C. as measured by the accumulation of the 114 KD product. Excision of the Vent IVPS2 was efficient at 65° C. but seems blocked at 80° C. Lack of accumulation may be due to thermal denaturation and precipitation of beta-galactosidase at 80° C. with time.

EXAMPLE 4

In-frame Insertion of IVPS in a PCR generated linear plasmid, such as one encoding beta-agarase I.

In example 2, we described inserting the IVPS cassettes from example 1 into a restriction enzyme linearized plasmid. This method is limited by the availability of appropriate restriction enzyme sites in a target gene. PCR amplification using opposing primers on a circular plasmid allows linearization of any plasmid at any position, limited only by the capacity of the PCR reaction. Once the target plasmid is linear, the process is essentially the same as described in example 2 for restriction enzyme generated linear plasmids.

As described in Example 2, insertion of an IVPS cassette into a target gene can be accomplished by ligation of an IVPS fragment with linear plasmid. In this example, PCR primers are used to generate plasmids linearized just prior to a serine or threonine codon. Thus, when the IVPS is excised and the two halves of the target protein are ligated, no extra amino acid is left behind in the target protein. The serine or threonine at the insertion site can be positioned on either the IVPS fragment or on the target gene fragment. If the serine or threonine is present on the IVPS cassette, then the target gene PCR primer can be constructed with a deletion of the 3 nucleotides encoding the first residue of the downstream EPS. If the IVPS cassette lacks the serine or threonine codon, then PCR with opposing, abutting PCR primers is used to synthesize target plasmid linearized at the serine or threonine codons.

This example describes cloning two IVPS elements, Vent IVPS2 and Deep Vent IVPS1, into a gene encoding beta-agarase I (Yaphe, W., Can. J. Microbiol. (1957) 3: 987–993) with-(Yaphe, W., Can. J. Microbiol. (1957) 3:987–993). by the procedure described in Example 2. The Deep Vent IVPS1 is inserted in front of a serine, the 108th codon, of the 290 amino acid beta-agarase I gene, while the Vent IVPS2 is inserted in front of a threonine, the 133th codon of the beta-agarase I gene.

The IVPS DNA fragments, including the serine codon (for Deep Vent IVPS1) or the threonine codon (for Vent IVPS2) at the 3' end, were prepared as described in Example 1. pAG6al (NEB), a 3.8 Kb recombinant plasmid containing the beta-agarase I gene sequence in vector pUC18 in the orientation of lac promoter, was used as a PCR template to synthesize linear plasmid DNA fragments. Primers agaS108.rv (5'-GAGAACTTTGTTCGTACCTG-3') (SEQ ID NO:8) and agaS108.fw (5'-GGTATTATTTCT-TCTAAAGCA-3') (SEQ ID NO:9) are compementary to DNA sequence 5' and 3' of the 108th codon, respectively. Primers agaT133 .rv (5'-GTTGTTTGTTGGTTTTACCA-3') (SEQ ID No:10) and agaT133.fw ( 5'-ATGGCAAAT-GCTGTATGGAT-3') are complementary to sequence 5' and 3' of the 133th codon, respectively. Each pair of the primers was used to synthesize linear plasmid DNA fragments, lacking the serine or threonine codon. The PCR mixture contained Vent DNA polymerase buffer (NEB), supplemented with 2 mM Magnesium sulfate, 400 uM of each dNTP, 0.5 uM of each primer, 20 ng plasmid DNA and 2 units of Vent DNA polymerase in 100 ul. Amplification was carried out using a Perkin-Elmer/Cetus thermal cycler at 94° C. for 30 sec, 45° C. for 30 sec and 72° C. for 5 min for 30 cycles. The PCR samples were extracted with phenol and chloroform, precipitated in 0.3M NaAcetate and 50% isopropanol, recovered by spinning at 10K for 10 min in a microfuge, dried and resuspended in 100 ul of distilled water. The DNA samples were then electrophoresed on a 1% low melting agarose gel and PCR-synthesized fragments were recovered as described in Example 1.

Ligation of PCR-synthesized fragment with phosphorylated IVPS fragment (Example 1) was carried out at 16° C. for 12 hours in 20 ul volume with addition of 9.5 ul distilled water, 2 ul of 10×T4 DNA ligase buffer (NEB), 4 ul of 0.01 ug/ul PCR-synthesized plasmid DNA, 4 ul IVPS DNA (0.20 ug of Vent IVPS2 or 0.32 ug Deep Vent IVPS1) and 0.5 ul of 400,000 U/ml of T4 DNA ligase (NEB). Transformation of E. coli strain RR1 with the ligation samples was performed as described in Example 2. Transformants were cultured in LB medium, supplemented with 100 ug/ml ampicillin, for extraction of plasmid DNA using alkaline lysis method Sambrook et al., Molecular Cloning-a laboratory manual (1989), Cold Spring Harbor Laboratory press, Cold Spring Harbor, N.Y.). Plasmid DNAs were compared with pAG6al by electrophoresis on a 0.8% agarose gel followed by staining with ethidium bromide. Recombinant plasmid pAG108S18 contains the Deep Vent IVPS1 insert while pAG133T22, 26, 31 and 35 all contain the Vent IVPS2 insert. Expression of the IVPS-beta-agarase I fusion genes.

Figure 5:
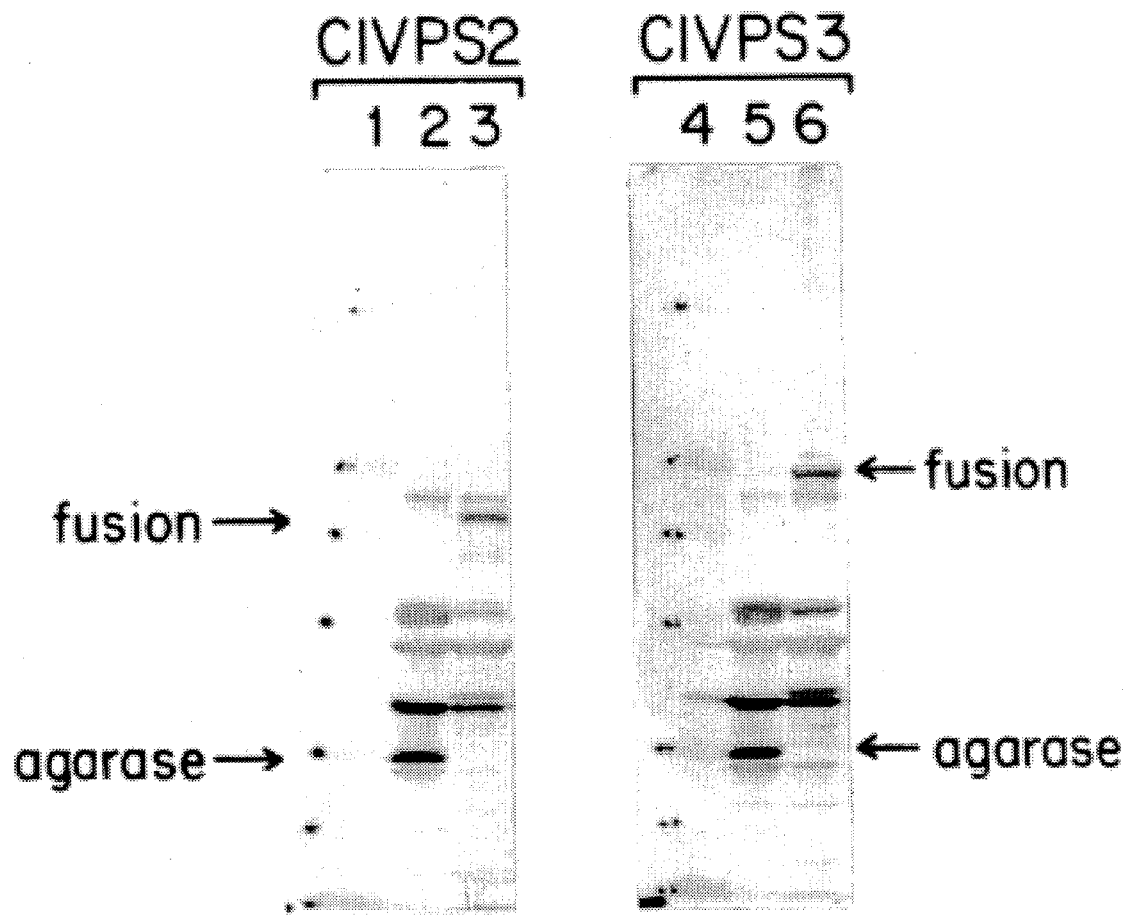
FIG. 5 shows by western blot examination of cell extracts with sera directed against beta-agarase, the detection of modified beta-agarase fusion protein. Lanes 1 & 4: size markers; Lanes 2 & 5,:beta-agarase standard; lane 3: CIVPS2-beta-agarase fusion; lane 6: CIVPS3-beta-agarase fusion.

The clones were further examined by their ability to express fusion proteins. RR1 cells carrying pAG108S18 or pAG133t35 were cultured in 1 liter of a modified LB medium, lacking dextrose, supplemented with 100 ug/ml ampicillin, at 30° C. until $OD_{600nm}$ reached about 0.5. After addition of inducer IPTG to a final concentration of 0.3 mM, the cultures were cooled down and grown at 25° C. for 4 additional hours. Cells were spun down and resuspended in 50 ml LB medium. Crude extracts were prepared as described in Example 3. Western blots using antibodies raised against I-Tli-I (NEB), I-PspI (NEB) and beta-agarase I (NEB) were performed to detect fusion (modified) proteins expressed from these clones. Samples were electrophoresed on 4–20% SDS gels (ISS, Daichi, Tokyo, Japan) with prestained markers (BRL), transferred to nitrocellulose, probed with antisera (from mouse), and detected using alkaline phosphate-linked anti-mouse secondary antibody as described by the manufacturer (Promega). Both anti-I-PspI sera and anti-beta-agarase I sera reacted with a 90–95 KDa product expressed from pAG108S18/RR1, of the expected size for a Deep Vent IVPS1 (approximately 60 KDa) —beta-agarase I (approximately 30 KDa) fusion protein (FIG. 5). Both anti-I-Tli-I sera and anti-beta-agarase I sera reacted with a 70–75 KDa product,from pAG108S18/RR1, approximately the size expected for a Vent IVPS2 (42 KDa)—beta-agarase I fusion protein (FIG. 5).

EXAMPLE 5

Insertion of IVPS into target gene by creation of new restriction enzymes sites through silent substitutions.

In the previous examples, an IVPS cassette containing the entire IVPS sequence, with or without the first downstream EPS codon, was inserted into a blunt, linearized plasmid. It is also possible to create a restriction site by silent mutations (preserving the amino acid residue) near the ends of either the IVPS or the target gene.

Creation of a restriction site near the end of the IVPS.

Figure 6:
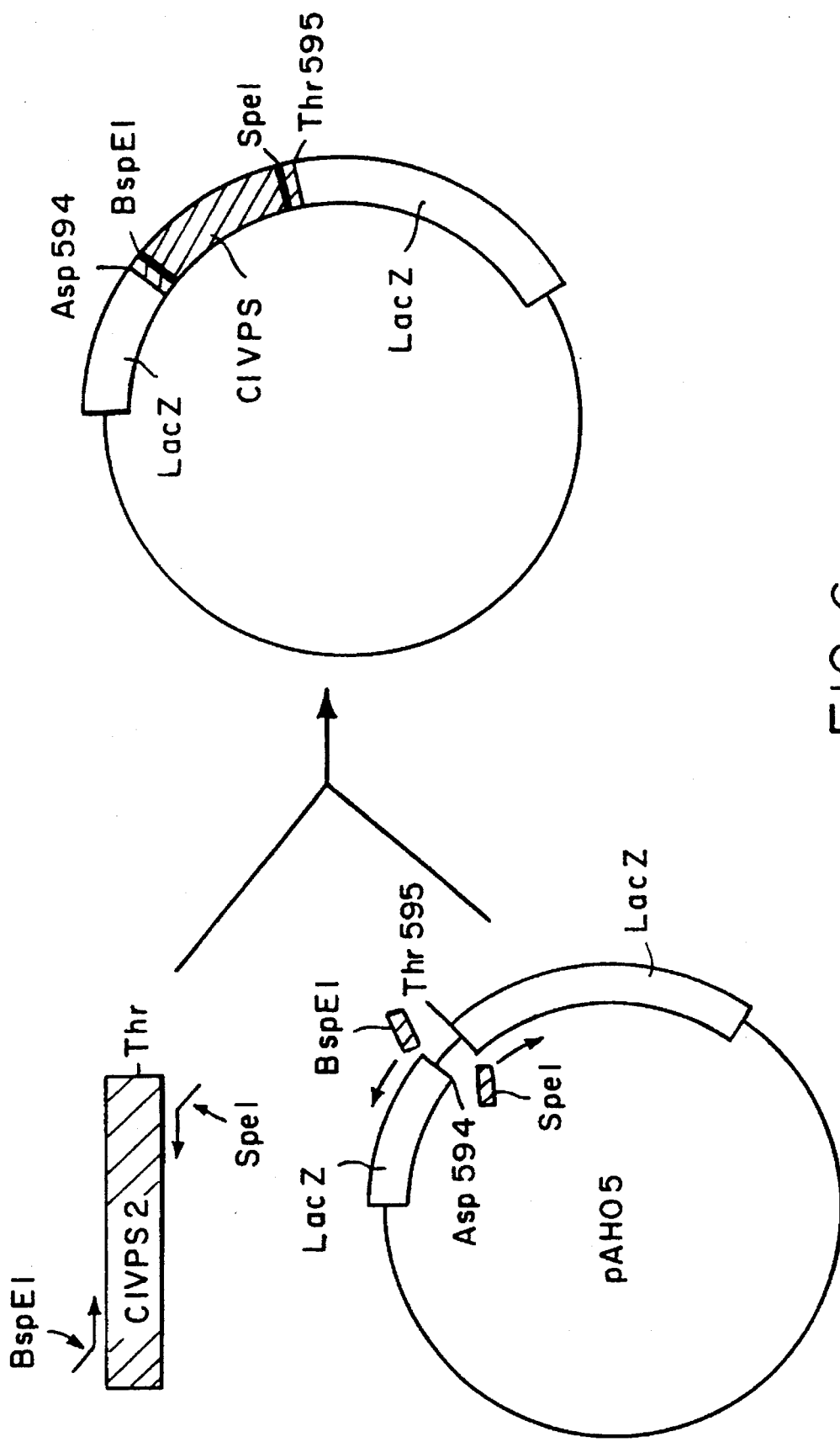
FIG. 6 illustrates insertion of IVPS2 (CIVPS2) into the beta-galactasidase gene by creation of new restriction sites (BspEI and SpeI) within the IVPS by silent mutations.

It is possible to create a restriction site by silent mutations (preserving the amino acid residue) at both ends of an IVPS to facilitate insertion of the IVPS at any position within the target gene. After creation of the new restriction sites, the IVPS is cut with these enzymes. The target gene plasmid is generated by PCR. Since the restriction sites are within the IVPS, one must include the missing IVPS sequences on the 5' end of the respective target gene PCR primers to complete the IVPS and to generate compatible cloning sites in the target gene (FIG. 6).

For example, silent mutations in Vent IVPS2 can create a BspEI site at the 5' end using primer Vent IVS2 Forward BspEI (5' AGTGTCTCCGGAGAAAGTGAGAT-3') (SEQ ID NO:12) and a SpeI at its 3' end, by using primer, Vent IVS2 Reverse SpeI (5' ATTGTGTACTAGTATGTTGTT GCAA(SEQ ID NO:113). It can then be inserted, for example, between an aspartic acid codon (residue 594) and a threonine codon (residue 595) within the lacZ coding region. A linear target gene plasmid can be generated by PCR as described in Example 4 with primers which include the BspEI and SpeI sites, the remaining portion of the IVPS and a region with identity to lacZ using primer, lacZ1/BspE1 reverse (5'-GCCTCCGGAGACACTATCG CCAAAAT-CACCGCCIGAA (SEQ ID NO:14)) and primer, lacZ2/SpeI forward (5'-GCCACTAGTACACAATACGECGAAC-GATCGCCAGTTCT(SEQ ID NO:15). DNA fragments are synthesized from both the IVPS and the target gene by PCR. Both IVPS and target gene primers contain the new restriction sites. After cutting with the appropriate restriction endonucleases, DNA fragments with compatible ends can then be ligated to create a fusion gene. Since no extra residue would be left after excision of the IVPS, native beta-galactosidase polypeptide would be expected to form if splicing occurs.

Insertion of IVPS at restriction sites near the insertion site.

In another general approach (FIG. 7), a restriction site near the insertion site in the target gene (for example, a threonine or a serine codon), can be used to insert an IVPS with ends compatible to the target gene. Restriction site(s) can be created by silent nucleotide substitution at or near the insertion site or native restriction sites can be used. A linear target gene plasmid is made by PCR as described in example 4, beginning at the restriction sites near the insertion site. The IVPS is synthesized with primers containing the compatible restriction sites and the remainder of the target gene sequence (the sequence between the restriction site and the insertion site). The IVPS DNA fragment, with the ends overlapping the sequence at the insertion site, can be synthesized, cut with the appropriate enzyme(s), and then ligated to the vector that is cut by the same enzyme(s).

Figure 7:
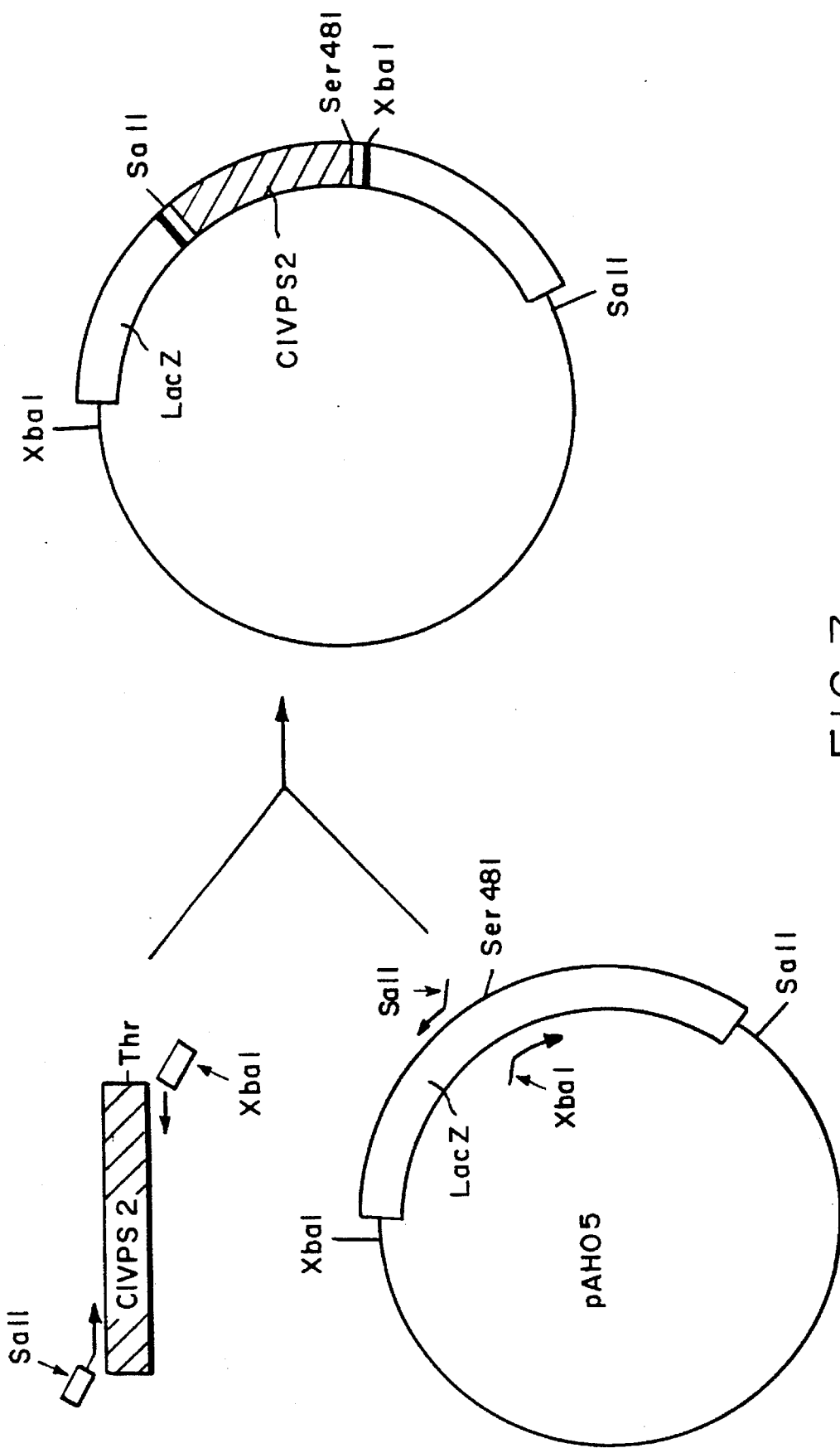
FIG. 7 illustrates insertion of either Deep Vent IVPS1 (CIVPS3) or Vent IVPS2 (CIVPS2) into the beta-galactasidase gene by creation of new restriction sites (XbaI and SalI) by silent mutations within the target gene.

For example, IVPS elements can be inserted between residue 479 (aspartic acid) and 481 (serine) within the lacZ gene by creating a SalI site (residues 478–479) and a XbaI site (residues 481–482 serine-arginine) by silent mutations. This can be achieved by PCR of the target plasmid, pAHO5, described in example 2, using primers, lacZ3 Sal reverse (5'-AGG GTC GAC AGA TTT GAT CCAGCG (SEQ ID NO:7) and lacZ4 Xba forward (5'-CCT TCT AGACCG GTGCAGTAT GAAGG (SEQ ID NO:16)). Next the IVPS2 fragment is generated by PCR using primers, Vent IVS2 Forward SalI (5'GCC GTC GACCCT AGTGTCTCA GGAGAA AGTGAG ATC (SEQ ID NO:17) and Vent IVS2 reverse XbaI 5'-GCCTCTAGA ATT GTG TAC CAG GAT GTTGTT TCC(SEQ. ID NO:18 ) DNA fragments are synthesized from both the IVPS and the target gene by PCR. Both IVPS and target gene primers contain the new restriction sites. Unfortunately, this vector also contains single XbaI and SalI sites (FIG. 7). Therefore, the target gene vector PCR product must be cut under conditions which produce partial digestion. The required linear plasmid is then isolated from agarose gels. After cutting with the appropriate restriction endonucleases, DNA fragments with compatible ends can then be ligated to create a fusion gene. Since no extra residue would be left after excision of the IVPS, native beta-galactosidase polypeptide would be expected to form if splicing occurs. Generally, it is important to select or create an unique site within the target gene and vector to facilitate the cloning process as described above.

EXAMPLE 6

Figure 8:
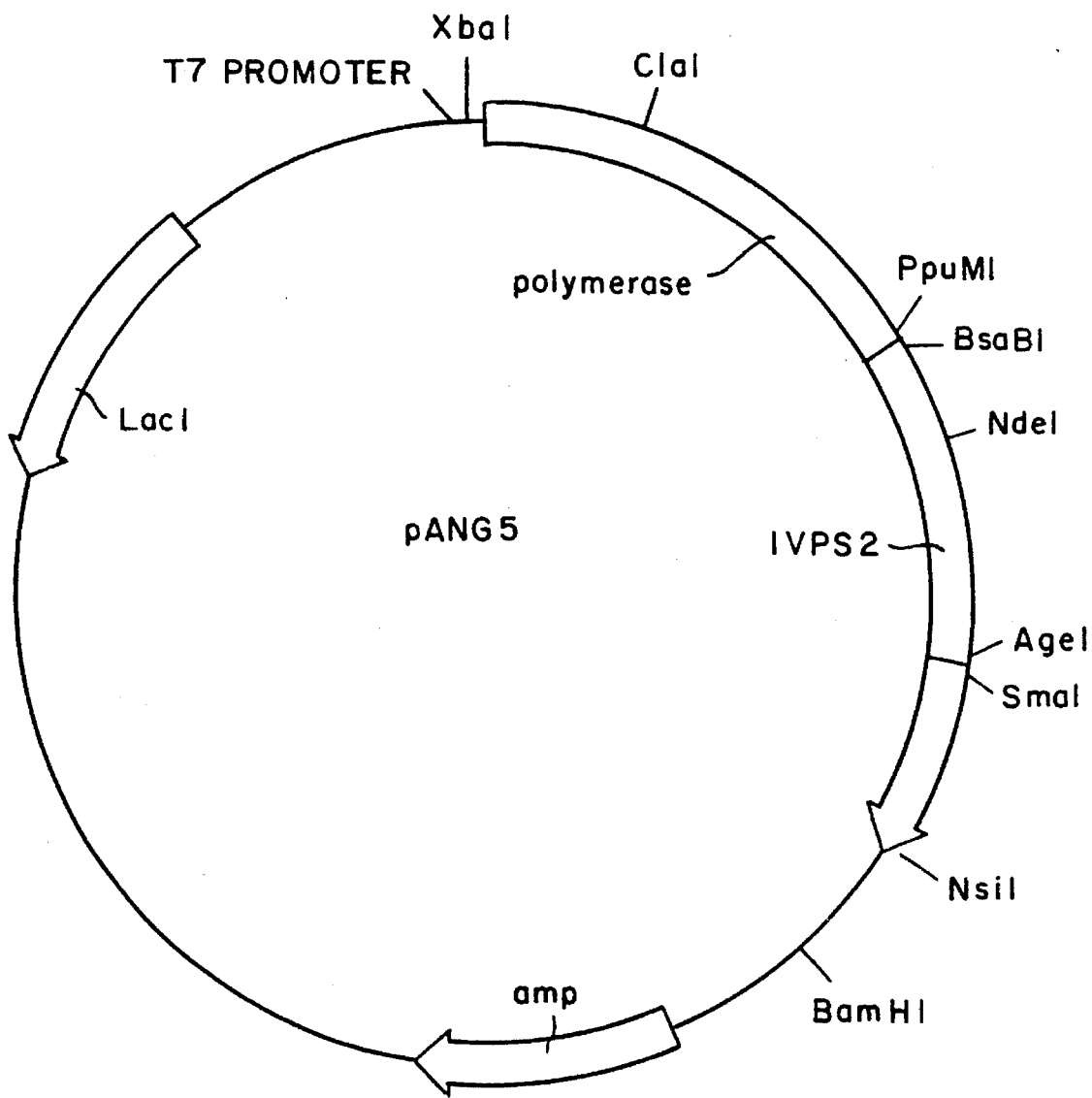
FIG. 8 is a plasmid map of pANG5.

A. To facilitate experimentation on the splicing of IVPS2 in Vent DNA polymerase, a modified version of the T7 promoter construct pV174-1B1 was created. This modified version, pANG5 (FIG. 8), encodes a Vent DNA polymerase precursor identical to that of pV174-1B1. Numerous silent mutations were introduced to simplify the generation of mutants as discussed in this application, particularly at the upstream and downstream splice junctions. Changes included:

1. Destroying XmaI and PpuMI sites in the vector backbone. The XmaI site was removed first by cutting the T7 expression vector pAII17 with XmaI, repairing the cohesive ends with the Klenow fragment of DNA polymerase I, and then religating the blunt termini. Plasmids were screened for resistance to cleavage by XmaI. The PpuMI site was similarly removed from the resulting vector, screening this time for resistance to PpuMI cleavage. The final vector was named pAML1. This vector allowed the use of unique XmaI and PpuMI sites within the polymerase gene.

2. Introduction of silent base changes to create restriction sites. Changes were introduced using oligonucleotide-directed mutagenesis as described by Kunkel (T. A. Kunkel, J. D. Roberts and R. A. Zakour, Methods in Enzymology (1987) 154, 367–382). Single-strand templates were created in two Bluescript SK- phagemid derivatives by superinfection with the f1 helper phage IR1 (Virology (1982) 122, 22–226). The first contained a BsaAI to BamHI fragment (representing nucleotides 3714–5837 of the Vent DNA polymerase sequence) from pV174-1B1 ligated into BamHI/EcoRV cut Bluescript. The second fragment included a ClaI to SspI fragment (nucleotides 816–4408) ligated into ClaI/EcoRV cut Bluescript.

The BsaAI/BamHI construct was mutagenized simultaneously with three oligonucleotides:

5'GC AAA GAA CCG GTG CGT CTC TTC 3' (SEQ ID NO:19) (AgeI nt 4669–4674)

5'A GCA ACA GAG TTA CCT CTT G 3' (SEQ ID NO:20) (amber1703ochre)

5' CA GTT TCC AGC TCC TAC AAT GAG ACC TAC GAG C 3' (SEQ ID NO:21) (D1236A)

where modified bases are underlined, and changes are indicated in parenthesis. The oligonucleotide to create D1236A also included silent base changes to create a BsaI site to assist in screening. The resulting isolate was named pAMN2.

The ClaI/SspI construct was mutagenized simultaneously with four oligonucleotides:

5' GTA GTG TCG ACC CCA TGC GG 3' (SEQ ID NO:22) (SalI nt 3863-3468)

5' C GTT TTG CCT GAT TAT TAT CTC ACT TTC 3' (SEQ ID NO:23) (BsaBI nt 3554-3563))

5' GTC CAC CTT CGA AAA AAG ATC C 3' (SEQ ID NO:24) (BstBI nt 3608-3613)

5' C CGC ATA AAG GAC CTT AAA GC 3' (SEQ ID NO:25) (PpuMI nt 3517-3523)

where markings are as above. Screening was also as above, with the resulting construct was named pAMO22.

Finally, the BsaAI/BamHI construct was also mutagenized with the oligonucleotide:

5' GAG GAA GAG ATC ATC ATC ATA GC 3' (SEQ ID NO:26) (BsaBI blocking nt 5641)

and screened for resistance to BsaBI cleavage due to the addition of a dam methylation site. The resulting construct was named pAMW3.

Finally, the NdeI site at the initiation codon of pV174-1B1 was inactivated by partial NdeI cleavage, repairing the termini with Klenow, and recircularizing using T4 DNA ligase. Plasmids were screened for the loss of the appropriate NdeI site. One such construct was named pAKC4.

The pANG5 construct was assembled from the above parts:

1. XbaI/ClaI from pAKC4 (translation initiation and amino terminus of vent DNA polymerase)
2. ClaI/NdeI from pAMO22 (more amino terminal polymerase plus the amino terminal region of IVPS2)
3. NdeI/NsiI from pAMN2 (carboxyl terminal region of IVPS2, carboxyl terminal region of vent DNA polymerase)
4. NsiI/BamHI from pAMW3 (final 5 amino acids of the polymerase plus the downstream region)
5. BamHI/XbaI from pAML1 (T7 promoter, origin of replication, ampicillin resistance).

Comparisons between pANG5 and the parent pV174-1B1 show identical patterns of Vent DNA polymerase and I-TliI production, with the exception of the greater viability of the pANG5 containing strains, as discussed below. This is as expected if splicing occurs at the protein level, as opposed to at the RNA or DNA level.

B. During work on the expression of the Vent DNA polymerase gene in *E. coli* it was found that a large increase in expression and cell viability occurred after deletion of IVPS1 and IVPS2. This increase could either represent toxic effects of I-TliII and I-TliI, the gene products of IVPS1 and IVPS2, respectively, or toxic effects of the splicing reaction itself. We reasoned that endonuclease and splicing activities could well be independent, allowing inactivation of the endonuclease without affecting splicing. Since we lacked knowledge of which amino acid residues were critical to endonuclease function, we chose a conserved residue within the amino-proximal dodecapeptide motif of I-TliI, the charged residue D1236, and made a single amino acid substitution to A as described in the construction of pANG5. Although these constructs expressed Vent DNA polymerase, no I-TliI activity was detected. Unlike pV174-1B1, T7 expression strains such as BL21(DE3) tolerated pANG5 well, even at 37° C. Analysis of protein splicing by western blot and pulse-chase analysis showed no discernible differences in protein splicing between pANG5 and pV174-1B1, namely production of a full-length precursor and subsequent formation of the mature polymerase and a protein corresponding in size to I-TliI.

C. A consensus calmodulin-dependent protein kinase II site (XRXXS*; Pearson et al., supra) was constructed, replacing tyrosine 1079 with arginine using cassette replacement mutagenesis. In short, pANG5 was cut at the unique sites BsaBI and PpuMI and the duplex (SEQ ID NO:27) listed below was inserted, introducing the desired change.

5'-GTCCTTCGTGCGGACAGTGTCTCAG-GAGAAAGTGAGATAA-3'.
3'-GAAGCACGCCTGTCACAGAGTC-CTCTTTCACTCTATT-5'.

The correct construct was verified by DNA sequencing.

D. Introduction of an amber stop codon for adding a blocked amino acid was accomplished by cassette replacement mutagenesis in pANG5. For example, serine 1082 was replaced by an amber codon using the following duplex (SEQ ID NO:28) inserted into pANG5 cut with PpuMI and BsaBI: 5'GTCCTTATCE-GACTAGGTCTCAGGAGAAAGTGAGATA-3'
3'GAA ATACGCCTGATCCAGAGTC-CTCTTTCACTTCTATT-5'.

Similarly, tyrosine 1472 was replaced with an amber termination codon by placing the following duplex (SEQ ID NO:29) into pANG5 cut with AgeI and SmaI:

5'CCGG TTCTTTGCAAACAACATCCTGGTACACAAT TAA GACGGC
3'AAGAAACGTTTGTTGTAGGACCATGTGT-TAATTCTGCCG
TTTTATGCCACA ATA CCC 3'
AAA ATACGGTGTTATGGG 5'

Finally, since the Vent DNA polymerase gene ends in an amber codon (TAG), that termination codon will be changed to an ochre codon (TAA) by inserting an appropriate restriction fragment from pAMN2 (described above) into the corresponding site in pANG5.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

We claim:

1. A modified protein comprising a target protein into which is inserted a controllable intervening protein sequence, wherein said controllable intervening protein sequence is capable of excision under predetermined conditions, and wherein said modified protein is non-naturally occurring.

2. The modified protein of claim 1, wherein the controllable intervening protein sequence renders the target protein substantially inactive.

3. The modified protein of claim 2, wherein upon excision of the controllable intervening protein sequence the activity of the target protein is substantially restored.

4. The modified protein of claim 1, wherein the controllable intervening protein sequence comprises for an endonuclease having homology to a homing endonuclease.

5. The modified protein of claim 4, wherein the endonuclease function of the controllable intervening protein sequence has been substantially inactivated.

6. The modified protein of claim 4, wherein the controllable intervening protein sequence is selected from the group consisting of CIVPS 1, 2, or 3.

7. The modified protein of claim 6, wherein the CIVPS is inserted immediately before a serine, threonine or cysteine residue of the target protein.

8. The modified protein of claim 6, wherein the CIVPS 1 is inserted immediately before a serine amino acid residue of the target protein.

9. The modified protein of claim 6, wherein the CIVPS 2 is inserted immediately before a threonine residue of the target protein.

10. The modified protein of claim 6, wherein the CIVPS 3 is inserted immediately before a serine amino acid residue of the target protein.

11. The modified protein of claim 6, wherein the CIVPS contains a serine, threonine or cysteine residue at its 3' end.

12. A method of producing a modified protein which comprises:
   (a) inserting a DNA encoding a controllable intervening protein sequence into a DNA encoding a target protein to form a fusion DNA;
   (b) expressing said fusion DNA to produce the modified target protein, 13. The method of claim 12, wherein the controllable intervening protein sequence DNA is inserted at a site appropriate for substantially decreasing the activity of the target protein.

14. The method of claim 13, wherein upon excision of the controllable intervening protein sequence the activity of the target protein is substantially restored.

15. The method of claim 12, wherein the controllable intervening protein sequence comprises an endonuclease having homology to a homing endonuclease.

16. The method of claim 15, wherein the endonuclease function of the controllable intervening protein sequence has been substantially inactivated.

17. The method of claim 12, wherein the controllable intervening protein sequence is selected from the group consisting of CIVPS 1, 2, or 3.

18. The method of claim 17, wherein the CIVPS is inserted immediately before a serine, threonine or cysteine residue of the target protein.

19. The method of claim 17, wherein the CIVPS 1 is inserted immediately before a serine amino acid residue of the target protein.

20. The method of claim 17, wherein the CIVPS 2 is inserted immediately before a threonine residue of the target protein.

21. The method of claim 17, wherein the CIVPS 3 is inserted immediately before a serine amino acid residue of the target protein.

22. The method claim 17, wherein the CIVPS contains a serine, threonine or cysteine residue at its 3' end.

23. A method of producing a protein comprising:
   (a) inserting a DNA encoding a controllable intervening protein sequence into a DNA encoding a target protein, wherein said controllable intervening protein sequence is capable of excision under predetermined conditions;
   (b) expressing the DNA of step (a) to produce a modified target protein; and
   (c) subjecting the modified target protein to conditions under which said controllable intervening protein sequence will undergo excision.

24. The method of claim 23, wherein insertion of the controllable intervening protein sequence renders the target protein substantially inactive.

25. The method of claim 24, wherein excision of the controllable intervening protein sequence substantially restores the activity of the target protein.

26. The method claim 23, wherein the controllable intervening protein sequence comprises an endonuclease having homology to a homing endonuclease.

27. The method of claim 26, wherein the endonuclease function of the controllable intervening protein sequence has been substantially inactivated.

28. The method of claim 23, wherein the controllable intervening protein sequence is selected from the group consisting of CIVPS 1, 2, or 3.

29. The method of claim 28, wherein the CIVPS is inserted immediately before a serine, threonine or cysteine residue of the target protein.

30. The method of claim 28, wherein the CIVPS 1 is inserted immediately before a serine amino acid residue of the target protein.

31. The method of claim 28, wherein the CIVPS 2 is inserted immediately before a threonine residue of the target protein.

32. The method of claim 28, wherein the CIVPS 3 is inserted immediately before a serine amino acid residue of the target protein.

33. The method of claim 28, wherein the CIVPS contains a serine, threonine or cysteine residue at its 3' end.

34. A method of producing a protein comprising:
   (a) producing a first modified protein comprising an amino portion of a target protein into which is inserted at its carboxy terminus a controllable intervening protein sequence;
   (b) producing a second modified protein comprising the remaining portion of the target protein of step (a) into which is inserted at its amino terminus a controllable intervening protein sequence; and
   (c) placing the first and second modified proteins under predetermined conditions appropriate for splicing of the controllable intervening protein sequence.

35. The method of claim 34, wherein the controllable intervening protein sequence inserted at the carboxy terminus of the target protein comprises an amino terminal fragment of the controllable intervening protein sequence and the controllable intervening protein sequence inserted at the amino terminus of the remaining portion of the target protein comprises the remaining fragment of the controllable intervening protein sequence.

36. A method of producing a protein comprising:
   (a) producing a first modified protein comprising a portion of a target protein into which a controllable intervening protein sequence is inserted at a splice junction; and
   (b) placing the first modified protein with the remaining portion of the target protein under predetermined conditions appropriate for splicing of the controllable intervening protein sequence.

\* \* \* \* \*

UNITED STATES PATENT AND TRADEMARK OFFICE
CERTIFICATE OF CORRECTION

PATENT NO. : 5,496,714

DATED : March 5, 1996

INVENTOR(S) : Comb, et al.

It is certified that error appears in the above-indentified patent and that said Letters Patent is hereby corrected as shown below:

Title page, and

Col. 1, line 2, replace "INTERVEINING" with --INTERVENING--

Column 3, line 67, replace "SEQ. ID 12" with --SEQ ID NO:2--

Column 8, line 60, replace "extremely_toxic" with --extremely toxic--

Column 12, line 26, replace "742,745" with --742, 745--

Column 15, line 63, replace "No:10" with --NO:10--

Column 17, line 20, replace "GCAA (SEQ ID NO:113)" with --TGCAA (SEQ ID NO:13)--

Column 17, line 28, replace "IGAA" with --GTAA--

Column 17, line 29, replace "ECGAAC" with --CCGAAC--

Column 18, line 1, replace "TCC" with --TGC--

Column 18, line 55, replace "CCG GTG" with --CCG GTG--

Column 18, line 57, replace "GAG TTA" with --GAG TTA--

Column 18, line 59, replace "AGC" with --AGC--

Column 18, line 59, replace "GAG ACC" with --GAG ACC--

UNITED STATES PATENT AND TRADEMARK OFFICE
CERTIFICATE OF CORRECTION

PATENT NO. : 5,496,714

DATED : March 5, 1996

INVENTOR(S) : Comb, et al.

It is certified that error appears in the above-indentified patent and that said Letters Patent is hereby corrected as shown below:

```
Column 19, line 1, replace "TCG ACC" with --TCG ACC--

Column 19, line 3, replace "GAT TAT TAT" with
     --GAT TAT TAT--

Column 19, line 5, replace "CGA AAA" with
     --CGA AAA--

Column 19, line 7, replace "GAC" with --GAC--

Column 19, line 13, replace "ATC" with --ATC--

Column 20, line 21, replace "CGT" with --CGT--

Column 20, line 23, replace "GCA" with --GCA--

Column 20, line 31, replace "GTCCCTTATCE-" with
     --GTCCTTTATGCG--

Column 20, line 32, replace "GACTAG" with
     --GACTAG--

Column 20, line 32, replace "ATA-3'" with --ATAA-3'--

Column 20, line 33, replace "ATC" with --ATC--

Column 20, line 34, replace "CTTCTATT-5'" with
     --CTCTATT-5'--

Column 20, line 39, replace "TAA" with --TAA--

Column 20, line 41, replace "ATT" with --ATT--
```

UNITED STATES PATENT AND TRADEMARK OFFICE
CERTIFICATE OF CORRECTION

PATENT NO. : 5,496,714

DATED : March 5, 1996

INVENTOR(S) : Comb, et al.

It is certified that error appears in the above-indentified patent and that said Letters Patent is hereby corrected as shown below:

Column 2, line 35, replace "galactasidase" with --galactosidase--

Column 2, line 65, replace "5,:" with --5:--

Column 3, line 2, replace "galactasidase" with --galactosidase--

Column 3, line 5-6, replace "galactasidase" with --galactosidase--

Column 3, line 54, replace "Sequencing Listing" with --Sequence Listing--

Column 6, line 23, replace "know" with --known--

Column 8, line 33, replace "chromatograph" with --chromatography--

Column 8, line 34-35, replace "chromatograph" with --chromatography--

Column 8, line 43, replace "know" with --known--

Column 9, line 19, replace "chromontography" with --chromatography--

Column 11, line 36, replace "NH4Ac" with --NH4Ac--

Column 11, line 43, replace "of10X" with --of 10X--

Column 12, line 55, replace "Daichi" with --Daiichi--

UNITED STATES PATENT AND TRADEMARK OFFICE
CERTIFICATE OF CORRECTION

PATENT NO. : 5,496,714
DATED : March 5, 1996
INVENTOR(S) : Comb, et al.

It is certified that error appears in the above-indentified patent and that said Letters Patent is hereby corrected as shown below:

Column 14, line 11, replace "followings" with --followed--

Column 15, line 60, replace "compementary" with --complementary--

Column 16, line 46, replace "Daichi" with --Daiichi--

Column 18, line 14, replace "an" with --a--

Column 19, line 26, replace "vent" with --Vent--

Column 19, line 30, replace "vent" with --Vent--

Signed and Sealed this

Ninth Day of July, 1996

*Attest:*

BRUCE LEHMAN

*Attesting Officer*    Commissioner of Patents and Trademarks